United States Statutory Invention Registration [19]

[11] Reg. Number: H22

Creasey et al. [45] Published: Feb. 4, 1986

[54] SYNERGISTIC EFFECT OF CHEMOTHERAPEUTIC AGENTS ON BETA-INTERFERON

[75] Inventors: Abla A. Creasey, Piedmont; Edward C. O'Rourke, Emeryville, both of Calif.

[73] Assignee: Cetus Corporation, Emeryville, Calif.

[21] Appl. No.: 663,672

[22] Filed: Oct. 22, 1984

[51] Int. Cl.[4] ..... A61K 39/00; A61K 45/02

[52] U.S. Cl. ..... 424/85; 435/811; 514/274

[58] Field of Search ..... 424/85, 251; 435/68, 435/811

[56] References Cited

PUBLICATIONS

Yamamoto et al., Cancer Letters, vol. 20, pp. 131–138, 1983.

Miyoshi et al., Cancer Letters, vol. 17, pp. 239–247, 1983.

Eppstein et al., Biochem. Biophys. Res. Comm., vol. 120, pp. 66–73, 1984.

*Primary Examiner*—Teddy S. Gron

*Attorney, Agent, or Firm*—Albert P. Halluin; Janet E. Hasak

[57] ABSTRACT

A composition of matter exhibiting a synergistic cytotoxic effect in combination therapy of certain breast cancer and myeloma cell lines is prepared by combining synergistically effective amounts of 5-fluorouracil and human recombinant beta-interferon, optionally together with a pharmaceutically effective diluent or carrier. Preferably the recombinant beta-interferon is a mutein in which the cysteine residue at position 17 of native beta-interferon is replaced by a serine residue.

18 Claims, 14 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIG._1.

```
                5                   10                  15                  20
MetSerTyrAsnLeu LeuGlyPheLeuGln ArgSerSerAsnPhe GlnCysGlnLysLeu
               25                  30                  35                  40
LeuTrpGlnLeuAsn GlyArgLeuGluTyr CysLeuLysAspArg MetAsnPheAspIle
               45                  50                  55                  60
ProGluGluIleLys GlnLeuGlnGlnPhe GlnLysGluAspAla AlaLeuThrIleTyr
               65                  70                  75                  80
GluMetLeuGlnAsn IlePheAlaIlePhe ArgGlnAspSerSer SerThrGlyTrpAsn
               85                  90                  95                 100
GluThrIleValGlu AsnLeuLeuAlaAsn ValTyrHisGlnIle AsnHisLeuLysThr
              105                 110                 115                 120
ValLeuGluGluLys LeuGluLysGluAsp PheThrArgGlyLys LeuMetSerSerLeu
              125                 130                 135                 140
HisLeuLysArgTyr TyrGlyArgIleLeu HisTyrLeuLysAla LysGluTyrSerHis
              145                 150                 155                 160
CysAlaTrpThrIle ValArgValGluIle LeuAgAsnPheTyr PheIleAsnArgLeu
              165                 170                 175                 180
ThrGlyTyrLeuArg Asn---
```

SYNERGISTIC EFFECT OF CHEMOTHERAPEUTIC AGENTS ON BETA-INTERFERON

BACKGROUND OF THE INVENTION

Field of the Invention

This invention relates to a composition of matter which exhibits a synergistic biological effect containing recombinant beta-interferon and 5-fluorouracil. More particularly, this invention relates to combination therapy exhibiting a synergistic cytotoxic effect on four breast carcinoma cell lines and one melanoma cell line.

Description of Related Disclosures

Interferons (IFN) constitute a group of naturally occurring proteins which ae known to exhibit antiviral, antitumor and immunoregulatory behavior. Two types of IFN have been identified based on differences in their observed biological properties and molecular structures: Type I and Type II. Beta-interferon ($\beta$-IFN) is a Type I IFN which can be induced in fibroblasts by viral challenge and contains about 165 amino acids. $\alpha$-IFN is also a Type I IFN inducible in leukocytes, and $\gamma$-IFN is a Type II IFN which is induced in lymphocytes in response to specific mitogenic stimuli and contains 146 amino acids.

After Paucker et al., *Virology*, 17, 324–334 (1962) showed that interferon suppressed the growth rate of mouse L cells, many investigators have studied treatment of mouse L cells with interferon and inhibition of tumor cell proliferation by interferon. See, e.g., Bordon, E. C., *Ann. Intern. Med.*, 91, 472–479 (1979).

Combination chemotherapy using two or more anticancer drugs to treat malignant tumors in humans is currently in use in research and in the clinic. The anticancer drugs may be antimetabolites, alkylating agents, antibiotics, general poisons, etc. Combinations of drugs are administered in an attempt to obtain a synergistic cytotoxic effect on most cancers, e.g., carcinomas, melanomas, lymphomas and sarcomas, and to reduce or eliminate emergence of drug-resistant cells and to reduce side effects to each drug.

It is known that Type I and Type II IFN's may be combined to produce a synergistic biological effect. See, for example, Fleishmann, W. R., *Cancer Res.*, 42, 869–875 (1982) and DeClercq, E., et al., *Cancer Letters*, 15, 223–228 (1982) (mouse IFN), work by Joan Schiller et al. at University of Wisconsin, Madison, Wisc., to be published under the title "Synergistic Antiproliferation Effects of Human Recombinant $\alpha$54, $\beta_{ser}$ and $\gamma$ Interferons on Human Cell Lines of Various Histogenesis" (human IFN) and European Patent Publication 107,498 published May 2, 1984 (human IFN).

In addition, Epstein, L. B., et al., *Ann. N.Y. Acad. Sci.*, 350, 228–244 (1980) reported that combination therapy consisting of interferon and other chemotherapeutic agents is more potently antineoplastic than interferon or chemotherapeutic agents alone in some malignancies such as ovarian cancer.

Sato, M., et al., *Int. J. Oral Surg.*, 13, 35–44 (1984) report that the growth inhibitory effects of a combination of the antimetabolite 5-fluorouracil (5-Fu) and native human alpha-interferon on the colony-forming ability of the human salivery gland adenocarbinoma cell line in an agar medium appeared to be syngeristic. 5-Fu was selected for use in the study as it appears to be used most commonly as an adjuvant and multi-drugs combination chemotherapy against malignant salivary gland neoplasms.

The cytotoxic action of 5-Fu was found to be potentiated by the concomitant application of interferon on human malignant tumor neoplastic cell lines in culture. See Miyoshi, T., et al., *Cancer Letters*, 17, 239–247 (1983) and Namba, M., et al., *Gann, 73, 814–824* (1982). Yamamoto et al., *Cancer Letters*, 20, 131—138 (1983) assessed sixteen drugs for potentiation of their cytotoxic effects by native beta-interferon (obtained from human fibroblasts by induction with PolyI:C) on a human neoplastic cell line, HeLa, derived from human uterine cervical carcinoma. Six of these drugs, including 5-Fu, had a specific additive or synergistic effect. All of the remainder of the drugs were ineffective. In addition, the growth of tumors from transplanted HeLa cells in nude mice was found to be suppressed in substantially greater degree by the combination treatment of 5-Fu and interferon than by treatment of either drug alone. Miyoshi, supra, and Namba, supra, have shown, however, that neither synergistic nor additive cytotoxic effects were detected in MCF-7 cells derived from a human mammary carcinoma by the combined treatment of 5-Fu and interferon.

Because human native interferon is expensive to extract, techniques have been developed for preparing recombinant forms of human interferon. Sugano et al., European Patent Publication No. 28,033 published June 6, 1981, have developd a technique for inserting a recombinant plasmid containing the human $\beta$-IFN gene into a host microorganism, preferably *E. coli*, to obtain a transformant which expresses recombinant $\beta$-IFN. Because the transformed *E. coli* contains multimers, purification and isolation of the IFN-$\beta$ is difficult. European Patent Publication No. 109,748 published May 30, 1984 describes a human $\beta$-IFN mutein (IFN-$\beta_{ser17}$) which has a cysteine residue at amino acid position 17 replaced by a serine residue to eliminate the problems of purification. Human IFN-$\beta_{ser17}$ has been combined with 9-[(1,3-dihydroxy-2-propoxy)methyl]-guanine to form a composition synergistically effective in inhibiting Herpes Simplex Virus-2, in work reported by Eppstein et al., *Biochemical and Biophysical Research Communications*, 120:66–73 (1984).

In view of the ineffectiveness of 5-Fu with native $\beta$-IFN in certain human mammary carcinoma cell lines, it would be useful to investigate whether 5-Fu is cytotoxically effective in combination with recombinant $\beta$-IFN in various human breast cancer cell lines and a melanoma cell line.

SUMMARY OF THE INVENTION

Accordingly, the present invention is directed to a composition having synergistic cytotoxic effect in breast cancer and melanoma cell lines which comprises synergistically effective amounts of 5-fluorouracil and recombinant human beta-interferon. The cell lines on which this combination is cytotoxically effective synergistically are the breast carcinoma cell lines CaMa-1, ZR-75-1, BT-20 and SK-BR-3 and the melanoma cell line Hs294T. Preferably the recombinant beta-interferon is produced by *E. coli* or Chinese hamster ovary cells. In a more preferred embodiment the recombinant beta-interferon is a mutein of native beta-interferon having the cysteine residue at position 17 of beta-interferon replaced by a serine residue. The shorthand designation for this mutein is IFN-$\beta_{ser17}$.

This invention is also directed to a process for preparing such a composition which comprises combining synergistically effective amounts of the two components.

In another embodiment the invention relates to an improved process for treating human breast cancer or melanoma with a composition of matter containing human beta-interferon wherein the improvement resides in treating tissue cultures of cell lines CaMa-1, ZR-75-1, BT-20, Hs294T or SK-BR-3 with a substantially pharmaceutically pure composition having synergistic cytotoxic effect comprising synergistically effective amounts of 5-fluorouracil and recombinant human beta-interferon.

A further aspect of the invention resides in the combined therapeutic composition which comprises said amounts of recombinant human beta-interferon and 5-fluorouracil as well as an effective amount of a pharmaceutically acceptable diluent or carrier.

BRIEF DESCRIPTION OF THE DRAWINGS

FIG. 1 is a diagram of the amino acid sequence of IFN-$\beta$.

DESCRIPTION OF THE PREFERRED EMBODIMENTS

Figure 2:
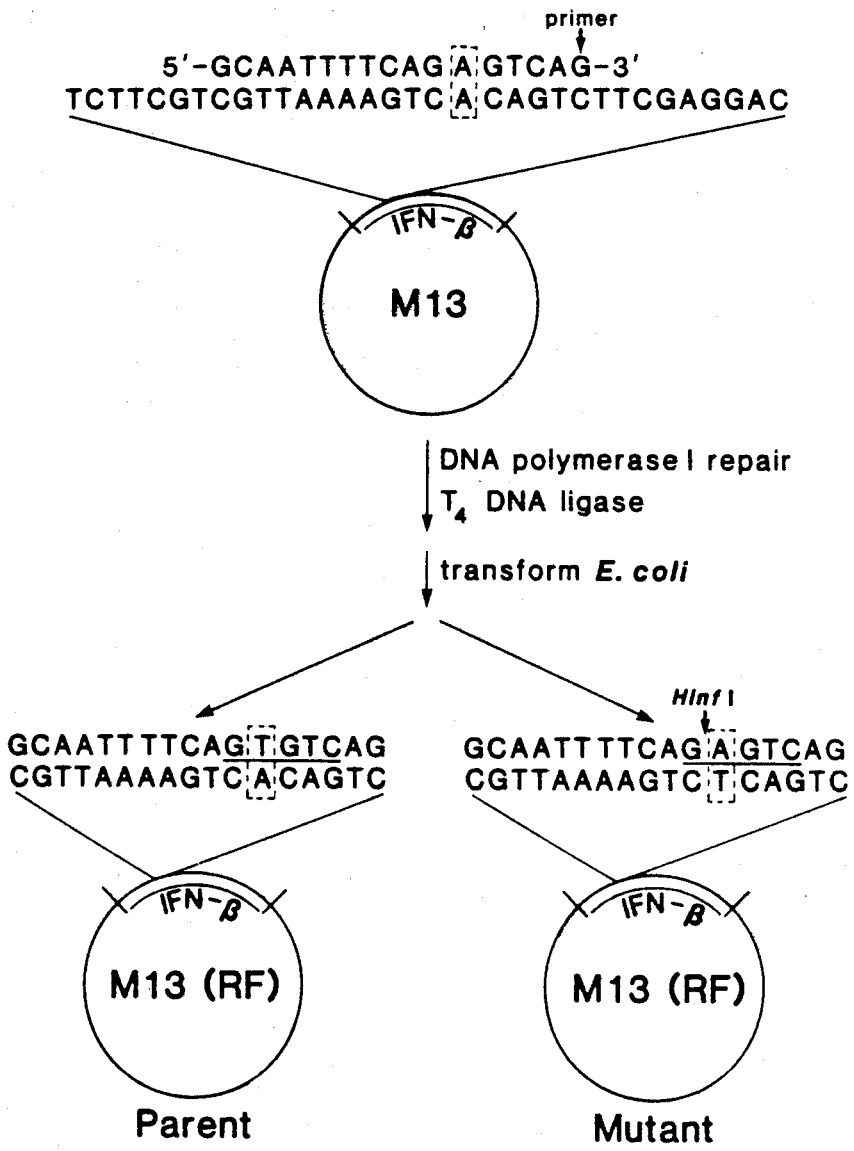
FIG. 2 is a schematic illustration showing the preparation of a mutant IFN-$\beta$ gene by oligonucleotide-directed mutagenesis.

By the term "recombinant human beta-interferon" is meant human beta-interferon produced by recombinant DNA techniques wherein generally the gene coding for human beta-interferon is cloned by known recombinant DNA technology such as by using human β-interferon messenger RNA as a template, the gene showing complementarity to human β-interferon messenger RNA is inserted in a suitable vector DNA such as an *E. coli* plasmid to obtain a recombinant plasmid, and the plasmid is used to transform a suitable host. The gene is expressed in the host to produce the recombinant protein. Examples of suitable recombinant plasmids include pBR322, pCR1, pMB9 and pSC1. The transformed host may be eucaryotic or procaryotic, and is preferably *E. coli* or Chinese hamster ovary cells. Techniques for preparing recombinant human IFN-β are described, for example, in EP 28,033 published June 6, 1981 to Sugano, et al. and U.K. 2,063,882 published June 10, 1981 to Revel, et al. In a preferred embodiment the recombinant human beta-interferon is a mutein of biologically active human beta-interferon in which cysteine residues which are not essential to biological activity have been deliberately deleted or replaced with other amino acids to eliminate sites for intermolecular crosslinking or incorrect intramolecular disulfide bond formation. Most preferably the mutein has the cysteine residue at position 17 of native beta-interferon replaced by a serine residue (designated IFN-$\beta_{ser17}$).

These muteins may be preparedd by using the oligonucleotide-directed mutagenesis procedure with a synthetic oligonucleotide primer that is complementary to the region of the IFN-β gene at the codon for cys 17 but which contains single or multiple base changes in that condon. A designer gene is produced that results in cys 17 being replaced with any other amino acid of choice. When deletion is desired the oligonucleotide primer lacks the codon for cys 17. Conversion of cys 17 to neutral acids such as glycine, valine, alanine, leucine, isoleucine, tyrosine, phenylalanine, histidine, tryptophan, serine, threonine and methionine is the preferred approach. Serine and threonine are the most preferred replacements because of their chemical analogy to cysteine. When the cysteine is deleted, the mature mutein is one amino acid shorter than the native parent protein or the microbially produced IFN-β.

The size of the oligonucleotide primer is determined by the requirement for stable hybridization of the primer to the region of the gene in which the mutation is to be induced, and by the limitations of the currently available methods for synthesizing oligonucleotides. The factors to be considered in designing olignonucleotides for use in oligonucleotide-directed mutagenesis (e.g., overall size, size of portions flanking the mutation site) are described by Smith, M. and Gillam, S., in *Genetic Engineering: Principles and Methods,* Plenum Press (1981) 3, 1–32. In general the overall length of the oligonucleotide will be such as to optimize stable, unique hybridization at the mutation site with the 5′ and 3′ extensions from the mutation site being of sufficient size to avoid editing of the mutation by the exonuclease activity of the DNA polymerase. Oligonucleotides used for mutagenesis in accordance with the present invention usually contain from about 12 to about 24 bases, preferably from about 14 to about 20 bases, and still more preferably from about 15 to about 18 bases. They will usually contain at least about three bases 3′ of the altered or missing codon.

The method for preparing the modified IFN-β gene broadly involves inducing a site-specific mutagenesis in the IFN-β gene at codon 17 (TGT) using a synthetic nucleotide primer which omits the codon or alters it so that it codes for another amino acid. When threonine replaces the cysteine and the primer is hybridized to the antisense strand of the IFN-β gene, the preferred nucleotide primer is GCAATTTTCACTCAG (underlining denotes the altered codon). When it is desirable to delete cysteine, the preferred primer is AGCAATTTTCAGCAGAAGCTCCTG, which omits the TGT codon for cys. When cysteine is replaced by serine, a 17-nucleotide primer, GCAATTTTCAGAGTCAG, which includes an AGT codon for serine is the primer of choice. The T⟶A transition of the first base in the cys 17 codon results in changing cysteine to serine. It must be recognized that when deletions are introduced, the proper reading frame for the DNA sequence must be maintained for expression of the desired protein.

The primer is hybridized to single-stranded phage such as M13, fd, or 0X174 into which a strand of the IFN-β gene has been cloned. It will be appreciated that the phage may carry either the sense strand or antisense strand of the gene. When the phage carries the antisense strand the primer is identical to the region of the sense strand that contains the codon to be mutated except for a mismatch with that codon that defines a deletion of the codon or a triplet that codes for another amino acid. When the phage carries the sense strand the primer is complementary to the region of the sense strand that contains the codon to be mutated except for an appropriate mismatch in the triplet that is paired with the codon to be deleted. Conditions that may be used in the hybridization are described by Smith, M. and Gillam, S., supra. The temperature will usually range between about 0° C. and 70° C., more usually about 10° C. to 50° C. After the hybridization, the primer is extended on the phage DNA by reaction with DNA polymerase I, $T_4$ DNA polymerase, reverse transcriptase or other suitable DNA polymerase. The resulting dsDNA is converted to closed circular dsDNA by treatment with a DNA ligase such as $T_4$ DNA ligase. DNA molecules containing single-stranded regions may be destroyed by Sl endonuclease treatment.

The resulting mutational heteroduplex is then used to transform a competent host organism or cell. Replication of the heteroduplex by the host provides progeny from both strands. Following replication the mutant gene may be isolated from progeny of the mutant strand, inserted into an appropriate expression vector, and the vector used to transform a suitable host organism or cell. Preferred vectors are plasmids pBR322, pCR1, and variants thereof, synthetic vectors and the like. Suitable host organisms are *E. coli*, Pseudomonas, *Bacillus subtilis*, *Bacillus thuringiensis*, various strains of yeast, *Bacillus thermophilus*, animal cells such as mice, rat or Chinese hamster overy (CHO) cells, plant cells, animal and plant hosts and the like. It must be recognized that when a host of choice is transformed with the vector, appropriate promoter-operator sequences are also introduced in order for the mutein to be expressed. Hosts may be prokaryotic or eukaryotic (processes for inserting DNA into eukaryotic cells are described in PCT applications nos. US81/00239 and US81/00240 published Sept. 3, 1981). *E. coli* and CHO cells are the preferred hosts. The muteins obtained in accordance with the present invention may be glycosylated or unglycosylated depending on the glycosylation occurring in the host organism used to produce the mutein. If desired, unglycosylated mutein obtained when *E. coli* or a Bacillus is the host organism may be optionally glycosylated in vitro by chemical, enzymatic and other types of modifications known in the art.

In the preferred embodiment of the subject invention respecting IFN-$\beta_{ser17}$ the cysteine residue at position 17 in the amino acid sequence of IFN-$\beta$, as shown in FIG. 1, is changed to serine by a T→A transition of the first base of codon 17 of the sense strand of the DNA sequence which codes for the mature IFN-$\beta$. The site-specific mutagenesis is induced using a synthetic 17-nucleotide primer GCAATTTTCAAGTCAG which is identical to a seventeen nucleotide sequence on the sense strand of IFN-$\beta$ in the region of codon 17 except for a single base mismatch at the first base of codon 17. The mismatch is at nucleotide 12 in the primer. It must be recognized that the genetic code is degenerate and that many of the amino acis may be encoded by more than one codon. The base code for serine, for example, is six-way degenerate such that the codons, TCT, TCG, TCC, TCA, AGT, and ACG all code for serine. The AGT codon was chosen for the preferred embodiment for convenience. Similarly, threonine is encoded by any one of codons ACT, ACA, ACC and ACG. It is intended that when one codon is specified for a particular amino acid, it includes all degenerate codons which encode that amino acid. The 17-mer is hybridized to single-stranded M13 phage DNA which carries the antisense strand of the IFN-$\beta$ gene. The oligonucleotide primer is then extended on the DNA using DNA polymerase I Klenow fragment and the resulting dsDNA is converted to closed circular DNA with $T_4$ ligase. Replication of the resulting mutational heteroduplex yields clones from the DNA strand containing the mismatch. Mutant clones may be identified and screened by the appearance or disappearance of specific restriction sites, antibiotic resistance or sensitivity, or by other methods known in the art. When cysteine is substituted with serine, the T→A transition, shown in FIG. 2, results in the creation of a new HinfI restriction site in the structural gene. The mutant clone is identified by using the oligonucleotide primer as a probe in a hybridization screening of the mutated phage plaques. The primer will have a single mismatch when hybridized to the parent but will have a perfect match when hybridized to the mutated phage DNA, as indicated in FIG. 2. Hybridization conditions can then be devised where the oligonucleotide primer wll preferentially hybridize to the mutated DNA but not to the parent DNA. The newly generated HinfI site also serves as a means of confirming the single base mutation in the IFN-$\beta$ gene.

The M13 phage DNA carrying the mutated gene is isolated and spliced into an appropriate expression vector, such as plasmid pTrp3, and a competent subvariant of *E. coli* strain MM294, designated MM294-1, may be transformed with the vector. Suitable growth media for culturing the transformants and their progeny are known to those skilled in the art. The expressed mutein of IFN-62 is isolated, purified and characterized. A preferred transformant was deposited under ATCC No. 39,517 on Nov. 18, 1983.

One method by which recombinant human beta-interferon useful herein may be purified from the transformed host which has been fermented in appropriate media is shown in the following scheme:

1. Concentration of the harvest material
2. Disruption of the cell suspension
3. Extraction of the cells with 2-butanol
4. Acid precipitation
5. Chromatographic purification using S-200 pre-column
6. Oxidation using iodosobenzoic acid
7. Passage through S-200 main column
8. Passage through G-75 column
9. Desalting on G-25 column
10. Formulation with normal serum albumin and dextrose
11. Lyophilization The above process enables yields of beta-interferon of greater than 95% purity.

The term "pharmaceutically pure" refers to recombinant beta-interferon as defined above which is suitable for unequivocal biological testing as well as for appropriate administration to effect treatment of a human patient. Substantially pharmaceutically pure means at least about 90% pharmaceutically pure.

The expression "synergistically effective amounts" of recombinant human beta-interferon and 5-Fu refers to amount of each component of the mixture which are effective in producing more than the additive effect of each component in the specific cell lines of this invention. The difference between additivity and synergism is often difficult to ascertain. Synergy is defined herein in terms of the fractional inhibitory concentration (FIC) index, which is the sum of the FIC's for the individual drugs used in each combination, as described by Sande et al., p. 1080–1105 in A. Goodman et al., ed., *The Pharmacological Basis of Therapeutics*, MacMillan Publishing Co., Inc., New York (1980). Under a strict scientific, and preferred, definition synergy is defined by a FIC index of less than 0.5, i.e., when 50% inhibition results from a combination of one-fourth or less of the concentration of each drug required to elicit the same effect if used individually (i.e., the minimal inhibiting concentration (MIC) of each drug). An FIC index of 0.5 under this strict definition defines an additive response. Under a broader definition used for purposes herein synergistically effective amounts are defined by an FIC index of less than 1.0, i.e., when 50% inhibition results from a combination of one-half or less of the MIC of each drug. An FIC index of 1.0 under this broader definition defines an additive response. Under this test, isobolograms may be prepared from the dose response curves for various combinations of β-interferon and 5-fluorouracil in each cell line, with synergy indicated by points below the line which line connects the FIC index of 1 for 5-Fu with the FIC index of 1 for IFN-β. This standard allows one to determine the MIC's for the combinations tested, so as to provide the MIC of each component needed to achieve a synergistic mixture. The exact amounts will depend, for example, on the particular cell line and the type of IFN-β employed.

Figure 3:
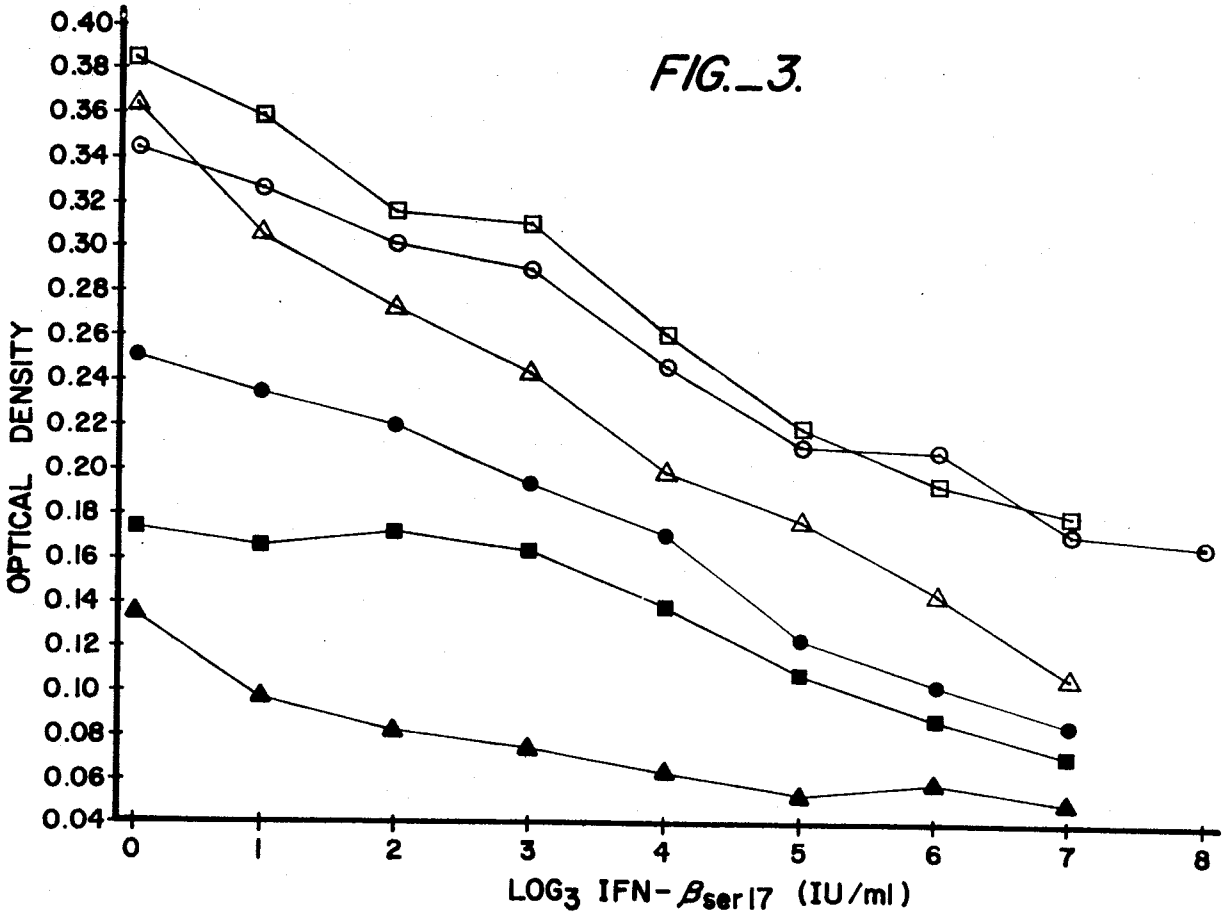
FIG. 3 is a series of dose response curves for CaMa-1 cells. At three days after cells were seeded culture fluids were replaced with fresh media containing IFN-$\beta_{ser17}$ in combination with 0 $\mu$g/ml 5-Fu (open dots), 0.016 $\mu$g/ml 5-Fu (open squares), 0.08 $\mu$g/ml 5- Fu (open triangles), 0.4 $\mu$g/ml 5-Fu (solid dots), 2 $\mu$g/ml 5-Fu (solid squares), and 10 $\mu$g/ml 5-Fu (solid triangles). At six days after these combinations were added, the optical density of the media was measured.
Figure 4:
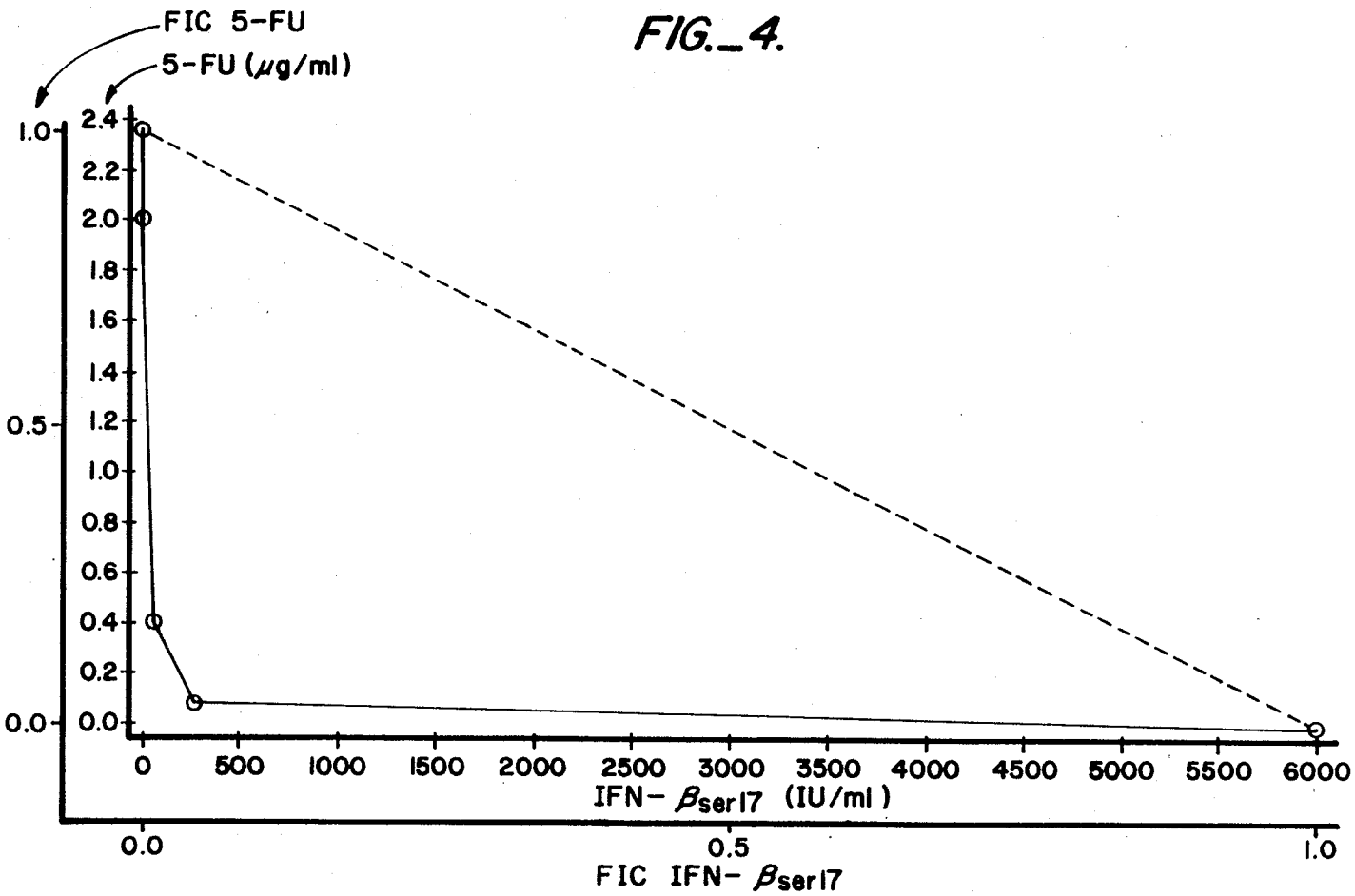
FIG. 4 is an isobologram drawn from 50% cell growth inhibitory concentrations obtained from the dose response curves of FIG. 3 of 5-Fu and IFN-$\beta_{ser17}$ individually and in combinations (open dots). The dashed lines represents an additivity line under the broad definition of synergy described below, with open dots below the line indicating synergy. The axes indicate both actual amounts of IFN-$\beta_{ser17}$ and 5-Fu and the fractional inhibitory concentration (FIC) indices as described further hereinbelow to which they correspond.

Based on the bioassays conducted as described herein on the CaMa-1 cell line provided in FIGS. 3 and 4 one can deduce that synergistically effective amounts of IFN-$\beta_{ser17}$ may range from about 50 to about 6000 international units per ml of total composition and that synergistically effective amounts of 5-Fu may range from about 0.05 to about 2.4 μg per ml of total composition. It is found that the magnitude of synergy increases with higher doses of both components. The practitioner skilled in the art will recognize that actual dosages may vary within a relatively wide range because of inherent limitations in the above calculations and will be able, according to available skill in the art, to determine more precisely those amounts of the components which will be effective in producing synergistic results. For the other cell lines the synergistically effective amounts of each component may be determined in a similar manner.

The recombinant β-IFN and 5-Fu may be combined using any suitable technique or may be used sequentially by first adding β-IFN or 5-FU and then adding the other component in a reasonable time after addition of the first component, usually within 24 hours depending mainly on the cell line being treated.

As a combination these two components are found to be synergistically effective against five cell lines and additively effective against four cell lines, using the broad synergy test. The cell lines in which the combination of recombinant β-IFN and 5-Fu are chemotherapeutically and synergistically effective are CaMa-1, SK-BR-3, BT-20, ZR-75-1, and H s294T. The combination herein is synergistically effective under the more strict synergy test described above for the breast carcinoma cell lines CaMa-1, SK-BR-3 and ZR-75-1, but not for the cell lines BT-20 and Hs294T. Thus, the cell lines CaMa-1, SK-BR-3 and ZR-75-1 are preferred herein.

CaMa-1 is an adenocarcinoma, breast and pleural effusion cell line which was obtained from a caucasian female patient age 51 with blood type O+ and described by Fogh, J., et al., *J. Natl. Can. Inst.*, 58, 209–214 (1977). This cell line is available from Dr. Jorgen Fogh at the Sloan-Kettering Institute for Cancer Research, 145 Boston Post Rd., Rye, N.Y. 10580. SK-BR-3 is an adenocarcinoma of the breast, malignant pleural effusion cell line deposited with the American Type Culture Collection (ATCC), 12301 Parklawn Dr., Rockville, Md. 20852 U.S.A. under ATCC No. HTB 30. ZR-75-1 is a human breast carcinoma cell line deposited in the ATCC under ATCC No. CRL 1500. BT-20 is a human breast carcinoma cell line deposited in the ATCC under ATCC No. HTB 19.

The human melanoma cell line Hs294T in which the recombinant β-IFN/5-Fu combination is synergistically cytotoxically effective was initiated and cloned at the Cell Culture Department, Naval Biosciences Laboratory, Oakland, CA and is similarly available from the Biological Carcinogenesis Branch of National Cancer Institute of the National Institute of Health, Bethesda, Md. The origin, characteristics and cytogenetics of this line have been described by Creasey, et al., *In Vitro*, 15, 342 (1979) and Creasey, et al., *PNAS USA*, 77, 1471 (1980).

The cytotoxic effect of the combination of recombinant IFN-β and 5-Fu may be assayed by a method which measures the direct effect of the combination against the tumor cells, i.e., reflects the inhibition of growth of the cells or cell death by the combination and at the same time permits handling a large number of samples conveniently. This assay measures vital dye uptake (Neutral Red) by the cells, a parameter which correlates 100% with the cell number, which is the relevant criterion for measuring the anticancer effect.

Various doses of the recombinant inteferon-β and 5-Fu, independently or in combination, may be added to proliferating tumor cells and then the effect scored 3–6 days later. The optical density of the cultures following the dye uptake may be recorded and the data may be analyzed using the isobologram method as described by Berenbaum, *Adv. Cancer Res.*, 35, 269 (1980). The magnitude of the interaction between recombinant IFN-β and 5-Fu may then be recorded, and end effect values may be interpolated from dose response curves.

The combination herein is preferably employed for in vitro use in treating these tissue cultures. The combination, however, may also be effective for in vivo applications. Depending on theintended mode of administration in vivo the compositions used may be in the dosage form of solid, semi-solid or liquid such as, e.g., tablets, pills, powders, capsules, gels, ointments, liquids, suspensions, or the like. Preferably the compositions are administered in unit dosage forms suitable for single administration of precise dosage amounts. The compositions may also include, depending on the formulation desired, pharmaceutically acceptable carriers or diluents, which are defined as aqueous-based vehicles commonly used to formulate pharmaceutical compositions for animal or human administration. The diluent is selected so as not to affect the biological activity of the beta-interferon. Examples of such diluents are distilled water, physiological saline, Ringer's solution, dextrose solution, and Hank's solution. The same diluents may be used to reconstitute lyophilized beta-interferon. In addition, the pharmaceutical composition may also include other medicinal agents, pharmaceutical agents, carriers, adjuvants, nontoxic, nontherapeutic, nonimmunogenic stabilizers, etc. Effective amounts of such diluent or carrier will be amounts which are effective to obtain a pharmaceutically acceptable formulation in terms of solubility of components, biological activity, etc.

The compositions herein may be administered to human patients via oral, parenteral or topical administrations and otherwise systemic forms for anti-melanoma and anti-breast cancer treatment.

The examples which follow illustrate the embodiments of the invention. In these examples, all parts and percentages are by weight per volume and all temperatures in degrees Celsium unless otherwise noted.

EXAMPLE 1

This example illustrates the synergistic cytotoxic effect of IFN-$\beta_{ser17}$ and 5-fluorouracil on the breast carcinoma cell line CaMa-1.

IFN-$\beta_{ser17}$ is a microbially produced mutein of IFN-$\beta$ in which the cysteine residue at amino acid position 17 is replaced with a serine residue. IFN-$\beta_{ser17}$ has two remaining cysteine residues: one at position 31 and the other at position 141. In native IFN-$\beta$ the cysteines at positions 31 and 141 interact to form a disulfide bridge. The genetically engineered *E. coli* microorganism strain used in this example to produce IFN-$\beta_{ser17}$ was deposited in the American Type Culture Collection, 2301 Parklawn Dr., Rockville, Md. 20852 U.S.A. on Nov. 18, 1983 under accession number 39,517.

These genetically engineered *E. coli* were grown in the following medium:

| Ingredient | Approximate Initial Concentration |
|---|---|
| $Na_3$ Citrate.$2H_2O$ | 3 mM |
| $KH_2PO_4$ | 30 mM |
| $(NH_4)_2SO_4$ | 74 mM |
| $MgSO_4.7H_2O$ | 3 mM |
| $MnSO_4.H_2O$ | 46 μM |
| $ZnSO_4.7H_2O$ | 46 μM |
| $CuSO_4.5H_2O$ | 1-2 μM |
| L-tryptophan | 350 μM |
| $FeSO_4.7H_2O$ | 74 μM |
| thiamine.HCl | 0.002% |
| glucose | 0.5% |

Dow Corning Antifoam B, 25% solution, glucose, 50% solution, and KOH, 5N, were added on demand.

Temperature was maintained at 37±1° C., pH was maintained at 6.5±0.1 with 10% NaOH, and dissolved oxygen was maintained at 30% of air saturation. Optical density and residual glucose measurements were taken at 14 hours and at approximately one-hour intervals thereafter. Harvest was made when glucose comsumption reached 40±6 g/l (OD at 680 nM=10-11).

The harvested material was concentrated approximately three-fold by circulating it through a microporous cross-flow filter under pressure. The concentrated cells were diafiltered againat deionized water until the harvest material was concentrated 4-5 fold. The cells were then disrupted by passing them through a Manton-Gaulin high-pressure homogenizer at $4.1-5.5\times10^4$ kpa. After the initial pass through the homogenizer a buffer containing sodium dodecyl sulfate (SDS) and soduim phosphate was added to the homogenate to a final concentration of 2% SDS, 0.08 M sodium phosphate, and homogenization was continued for one hour at $4.1-5.5\times10^4$ kpa. Solid dithiothreitol (DTT) was then added to a final concentration of 50 mM and the homogenizate was heated to 90±5° C. for 10 minutes. The resulting cell suspension was cooled to ambient temperature and extracted with 2-butanol at a 1:1 2-butanol:suspension volume ratio by pumping the cell suspension and a 2-butanol separately but simultaneously through a static mixer. The mixture was then centrifuged and the 2-butanol rich phase containing the interferon was collected at room temperature and held at room temperature for about 16-18 hours.

The 2-butanol-rich phase was mixed with 2.5 volumes of 1.0% SDS in phosphate buffered saline (PBS). Solid DTT was added to a final concentration of 2 mM. The pH of the mixture was adjusted to 6.2±0.1 with glacial acetic acid and this mixture was centrifuged. The resulting paste was collected and then resuspended in PBS+10% SDS with pH adjustment to 8.5±0.1 using 1N NaOH. Solid DTT was added to a final concentration of 100 mM and the suspension was heated to 90±5° C. for 10 minutes. The suspension was then cooled to about 25° C., the pH was adjusted to 5.5±0.1 with glacial acetic acid, and the solution was filtered through a 0.45 μm filter.

The solution was then applied to a Sephacryl S-200 pre-column and the fractions containing highest interferon activities were pooled and concentrated using a hollow-fiber ultrafiltration unit with a 10 kdal molecular weight cut-off.

A 1 mM o-iodosobenzioc acid solution was prepared by mixing the acid in water, sonicating the mixture for about 5 minutes and then stirring and adding 2% NaOH slowly to obtain a final pH of 8.2±0.2 (additional sonication may be used as an alternative to adding base).

A reaction buffer medium was prepared by dissolving $Na_4P_2O_7$. 10 $H_2O$ in water to a concentration of 2 mM. The pH of this solution was adjusted to 9.0 by adding 10% acetic acid. SDS to 0.1%, ethylenediaminetetraacetic acid (EDTA) to 1 mM and the o-iodosobenzoic acid solution to $15\times10^{-6}$ M were added to the solution.

The buffer medium was placed in a reaction vessel equipped with a magnetic stirrer and a pH electrode set at 9.0. The IFN-$\beta_{ser17}$ preparation and the o-iodosobenzoic acid solutions were added to the reaction mixture from holding vessels using peristaltic pumps that were calibrated to introduce equivalent mol ratios of the IFN and oxidizing agent. The pH of the reaction mixture was controlled at 9.0 ±0.1 by adding 0.5N NaOH via a peristaltic pump at 5 ml/hr. as needed. The IFN-$\beta$ solution (5 mg/ml in 50 mM acetate buffer, pH 5.5) was added at a flow rate of 2 ml/hr. (7.0 micromole/hr.) for about 5 hours; the o-iodosobenzoic acid solution was added at 7 ml/hr. (7 micromole/hr.) over the same time period. The addition of the acid solution was continued thereafter to get a final excess of 10-15 mol. The reaction was followed by reverse-phase HPLC and by assaying the residual thiol content of IFN-$\beta_{ser17}$ by Ellman's assay. After 6.5 hours the reaction was terminated by adding 10% acetic acid to the reaction mixture to a pH of 5.5±0.2.

The IFN-$\beta_{ser17}$ was concentrated using a hollow fiber ultrafiltration unit with a 10K molecular weight cut-off.

A Sephacryl $S_{-200}$ main column was loaded with the concentrated IFN-$\beta_{ser17}$ and the fractions were collected into clean, deyrogenated vessels. SDS-PAGE was perfomed on samples from each fraction tube starting from the beginning of the peak to be pooled to the end of the peak. Using SDS-PAGE results the interferon fractions which contained no detectable high molecular weight contaminants were determined and pooled.

The Sephacryl main column pool was concentrated by using a hollow-fiber ultrafiltration unit with a 10K molecular weight cut-off.

A Sephadex G-75 column was loaded with the concentrated pool and the fractions were collected into clean, depyrogenated vessels. SDS-PAGE analysis was performed on samples from each fraction tube starting from the beginning of the peak to be pooled to the end of the peak. Using SDS-PAGE the fractions containing no detectable flow or high molecular weight contaminants were determined and pooled for desalting.

A Sephadex G-25 column was equilibrated with 1 mM sodium hydroxide and loaded with the Sephadex $G_{-75}$ pool using distilled water adjusted to pH 10.8-11 with 50% NaOH. The void volume peak was collected and the product was formulated within 15 minutes after desalting.

The volume of desalted material was measured and the mg of IFN to be formulated were calculated. The amount of normal serum albunim (human) USP (NSA) and 50% dextrose monohydrate USP required to meet the following specifications was calculated:

| IFN (mg/ml) | NSA (mg/ml) | Dextrose Monohydrate (mg/ml) |
|---|---|---|
| 0.25 | 12.5 | 12.5 |

The NSA was diluted with water for injection to yield a final concentration of 1.25%. The pH of the diluted NSA solution was raised to 12.0±0.5 with 10% NaOH. The IFN was added immediately to the NSA and the pH of the mixture was adjusted to 7.5±0.3 with 3-6N HCl. The calculated amount of dextrose was added. The formulated product was prefiltered through a 0.45 μm filter and the sterile filter was prefiltered through a 0.22 μm filter within 4 hours.

Vials, stoppers and components to be used for the aseptic filling operation were sterilized. The surfaces of sterile room and equipment were sanitized and the vials were filled to 1.2 ml volume.

Each tray of vials was placed onto a shelf in a lyophilizer and the appropriate thermocouples were attached to representative vials. The vials were frozen on the shelf to between −35° and −45° C. The lyophilization cycle was completed and the vials were mechanically sealed under vacuum in the chamber.

The vial contents including IFN-$\beta_{ser17}$ was then dissolved in 50 mM phosphate buffer, pH 7.0, 0.1% SDS at a concentration of 1.485 ng IFN/ml, filtered through a millipore-GS 0.22 μm syringe filter and stored in the dark at room temperature. Biological activity of the IFN was determined by the cytopathic effect (CPE) assay described by Stewart, W. E. II in *The Interferon System*, Springer-Verlag, New York, N.Y. (1981). The biological activity of the IFN was $2\times10^8$ IU/mg. The IFN concentrations were diluted in the media in which the cells were grown and aliquots of the dilutions were assayed by the CPE assay.

The 5-fluorouracil used in the experiments herein was obtained from Sigma Chemical Company. Solutions containing 10 mg/ml in water adjusted to pH 8.0 with NaOH were prepared and filtered through Nalgene 0.2 μm syringe filters immediately before use. Final concentration was based on absorbance at 260 nm of a 1:1000 dilution of the filtered solution. Dilutions of 5-fluorouracil used to treat the cells were made in the same medium in which the cells were grown.

The cytotoxic effect of IFN-$\beta_{ser17}$ and 5-Fu combinations was observed for nine cell lines, eight of which were breast carcinoma cell lines and one of which was a melanoma cell line. Cell lines SK-BR-3 (ATCC HTB 30),ZR-75-1 (ATCC CRL 1500), ZR-75-30 (ATCC CRL 1504), MCF-7 (ATCC HTB 22), BT-20 (ATCC HTB 19), T-47-D (ATCC HTB 133), and BT-549 (ATCC HTB 122) were obtained from the American Type Culture Collection. CaMa-1 is available from Dr. Jorgen Fogh of the Sloan-Kettering Institute for Cancer Research, 145 Boston Post Road, Rye, N.Y. 10580. Melanoma cell line Hs294T was obtained as described above and is also described by Creasey, et at., *In Vitro*, 15, 342 (1979).

All of these cell lines were plated at 5000 cells per well in 0.10 ml medium in 96-well plates (Falcon No. 3075). Because the cell lines grew at different rates they were treated according to different schedules. Hs294T was treated one day after plating and was harvested three days after treatment. The breast carcinoma cell lines were treated three days after plating and harvested six days after treatment. Dilutions of the agents 5-Fu and IFN-$\beta_{ser17}$ were made at four times the final concentration desired. These dilutions were mixed with equal volumes of medium or with equal volumes of the other agent. Then, 0.10 ml aliquots of the resulting solutions were added to the wells containing the cells. The cells were treated continuously with the agent or agents for the three-day or six-day period. Two to four replicate plates were done for each cell line. Concentrations of IFN-$\beta_{ser17}$ used ranged from 1 to 6000 IU/ml. Concentrations of 5-Fu used ranged from 0.01 to 100 μg/ml. The peak plasma concentration of 5-Fu in humans following in vivo administration of therapeutic doses is 26 to 123 μg/ml (Alberts, et al., p, 354, in Salmon, ed., *Cloning of Human Tumor Stem Cells*, Alan R. Liss, Inc., N.Y., 1980).

A solution of Neutral Red (C.I. 50040, Fisher Scientific Co. ) was prepared immediately before use by mixing 36 mg of the dye with 100 ml of phosphate buffered saline (PBS) and filtering the mixture through a 0.2 μm filter. A total of 50 μl of the dye solution was added to each well of cells growing in 0.20 ml medium per well in the 96-well plates. The plates were then incubated at 37° C. for 1 hour. The medium-dye solution was aspirated off and the cells were washed twice with warm PBS. A total of 0.18 ml of a 1:1 mixture of ethanol and 0.1M sodium monobasic phosphate was added to each well to solubilize the dye taken up by the cells. The plates were allowed to stand at room temperature until the dye was completely extracted from the cells and evenly distributed. Absorbance at 540 nm was measured in a Titertek Multiscan 96-well plate reader. Correlation of absorbance with number of cells was determined in independent experiments using BT-549 cells where the cell number versus the absorbance at 540 nm was plotted.

An isobole was constructed and an interaction index was calculated according to Berenbaum, *Adv. Cancer Res.*, 35, 269 (1980). These methods require the measurement of the same end effect for a number of different combinations. Despite the large number of combinations tested, a common end effect was seldom measured. Therefore, the end effect values were interpolated from dose response curves.

The dose response curves for CaMa-1 are shown in FIG. 3. These curves show the effect of adding increasing concentrations of IFN-$\beta_{ser17}$ at six fixed 5-Fu concentrations of 0.016, 0.08, 0.4, 2 and 10 μg/ml, with the open dot, square and triangle representing 0, 0.016 and 0.08, and the closed dot, square and triangle representing the 0.4, 2 and 10 5-Fu concentrations. Table 1 below provides interaction indices for various doses and whether they indicate synergism, an additive effect, or antagonism.

TABLE 1

Interaction Indices Calculated for CaMa-1*

| Dose of 5-Fu in Combination (μg/ml) | Dose of IFN-$\beta_{ser17}$ in Combination (IU/ml) 3 | 8 | 25 | 75 | 220 | 670 | 2000 |
|---|---|---|---|---|---|---|---|
| 0.016 | >1 | >2 | >5 | 1.4 | 1.3 | 0.85 | 1.0 |
| 0.08 | 1.0 | 0.48 | 0.49 | 0.21 | 0.12 | | |
| 0.4 | 0.74 | 0.59 | 0.34 | 0.19 | | | |
| 2.0 | 0.67 | | | | | | |

TABLE 1-continued

| Interaction Indices Calculated for CaMa-1* | | | | | | | |
|---|---|---|---|---|---|---|---|
| Dose of 5-Fu in Combination (μg/ml) | Dose of IFN-$\beta_{ser17}$ in Combination (IU/ml) | | | | | | |
| | 3 | 8 | 25 | 75 | 220 | 670 | 2000 |
| 10 | | | | | | | |

*>1 = antagonism; <1 = synergism; 1 = additive effect under broad test

These data show that within certain concentration ranges the combination of IFN-$\beta_{ser17}$ and 5-Fu is synergistic.

The dose response curves were used to prepare the isologram shown in FIG. 4, which demonstrates that for 50% growth inhibition for CaMa-1 the combination is synergistic both under the broad test of synergy and the stricter test.

Table 2 is an equivalence table comparing doses of single agents with doses of combinations which give equivalent inhibition of growth.

TABLE 2

| Concentrations of IFN-$\beta_{ser17}$ and 5-Fu, Used Alone or in Combination with Each Other, Required to Produce Different Levels of Growth Inhibition of CaMa-1 | | | | | |
|---|---|---|---|---|---|
| Percent Growth Inhibition Observed | Concentration Required When Agent Used Alone | | Concentrations Required When Agents Used in Combination | | Percent Growth Inhibition Expected If Combination Were Additive Under Broad Test |
| | IFN-β IU/ml | 5-Fu μg/ml | IFN-β IU/ml | 5-Fu μg/ml | |
| 7 | 3.7 | 0.13 | 8.1 | 0.016 | |
| 7 | 3.7 | 0.13 | 2.3 | 0.08 | |
| 19 | 33 | 0.32 | 52 | 0.016 | |
| 19 | 33 | 0.32 | 7.2 | 0.08 | |
| 30 | 100 | 0.47 | 140 | 0.016 | 33 |
| 30 | 100 | 0.47 | 30 | 0.08 | 20 |
| 30 | 100 | 0.47 | 2 | 0.4 | 27 |
| 42 | 1000 | 1.2 | 585 | 0.016 | 39 |
| 42 | 1000 | 1.2 | 81 | 0.08 | 29 |
| 42 | 1000 | 1.2 | 22 | 0.4 | 30 |
| 54 | 6000 | 3.2 | 280 | 0.08 | 38 |
| 54 | 6000 | 3.2 | 113 | 0.4 | 37 |

EXAMPLE 2

This example shows that the combination of 5-Fu and IFN-$\beta_{ser17}$ is synergistic for the cell line ZR-75-1.

Figure 5:
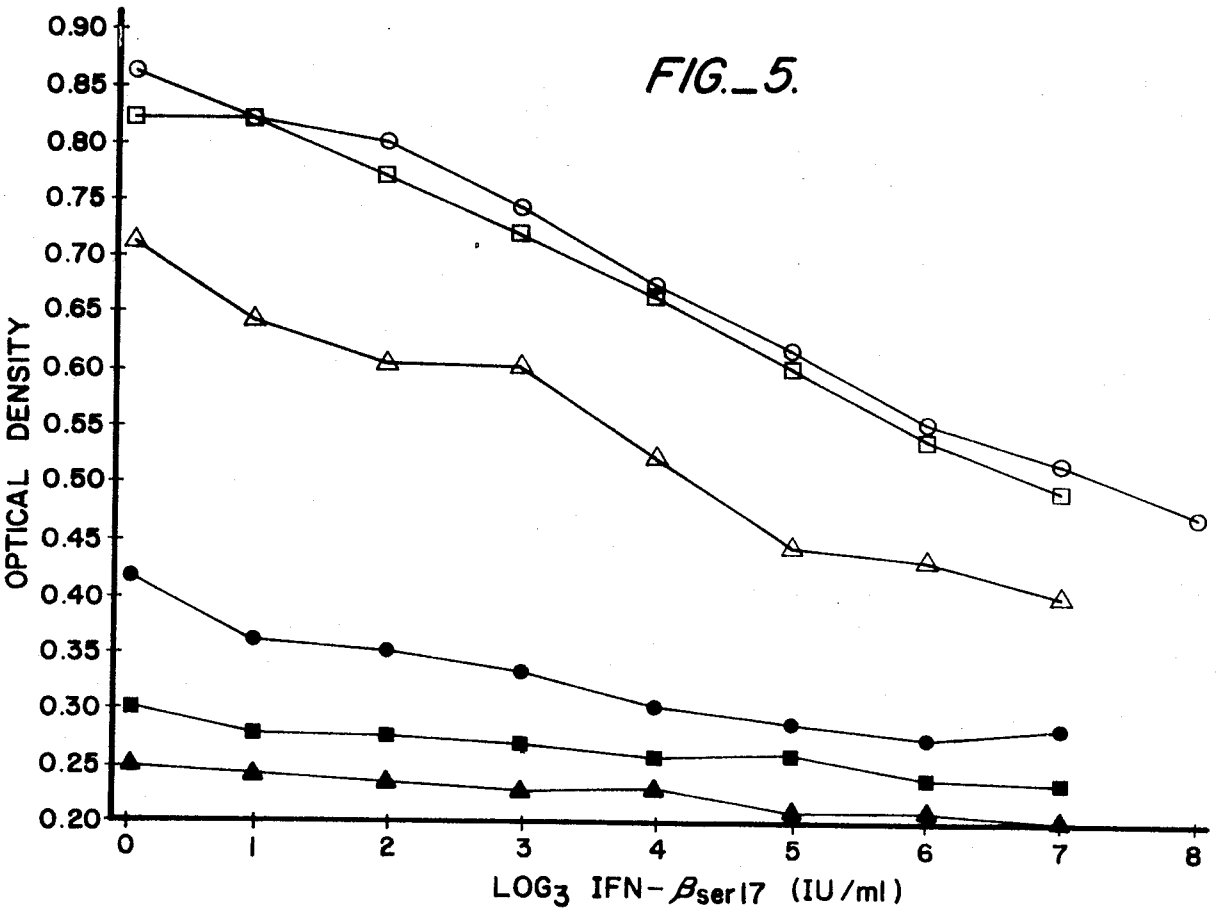
FIG. 5 is a series of dose response curves for ZR-75-1 cells. At three days after cells were seeded culture fluids were replaced with fresh media containing IFN-$\beta_{ser17}$ in combination with 0 $\mu$g/ml 5-Fu (open dots), 0.016 $\mu$g/ml 5-Fu (open squares), 0.08 $\mu$g/ml 5-Fu (open triangles), 0.4 $\mu$g/ml 5- Fu (solid dots), 2 $\mu$g/ml 5-Fu (solid squares), and 10 $\mu$g/ml 5-Fu (solid triangles). At six days after these combinations were added, the optical density of the media was measured.
Figure 6:
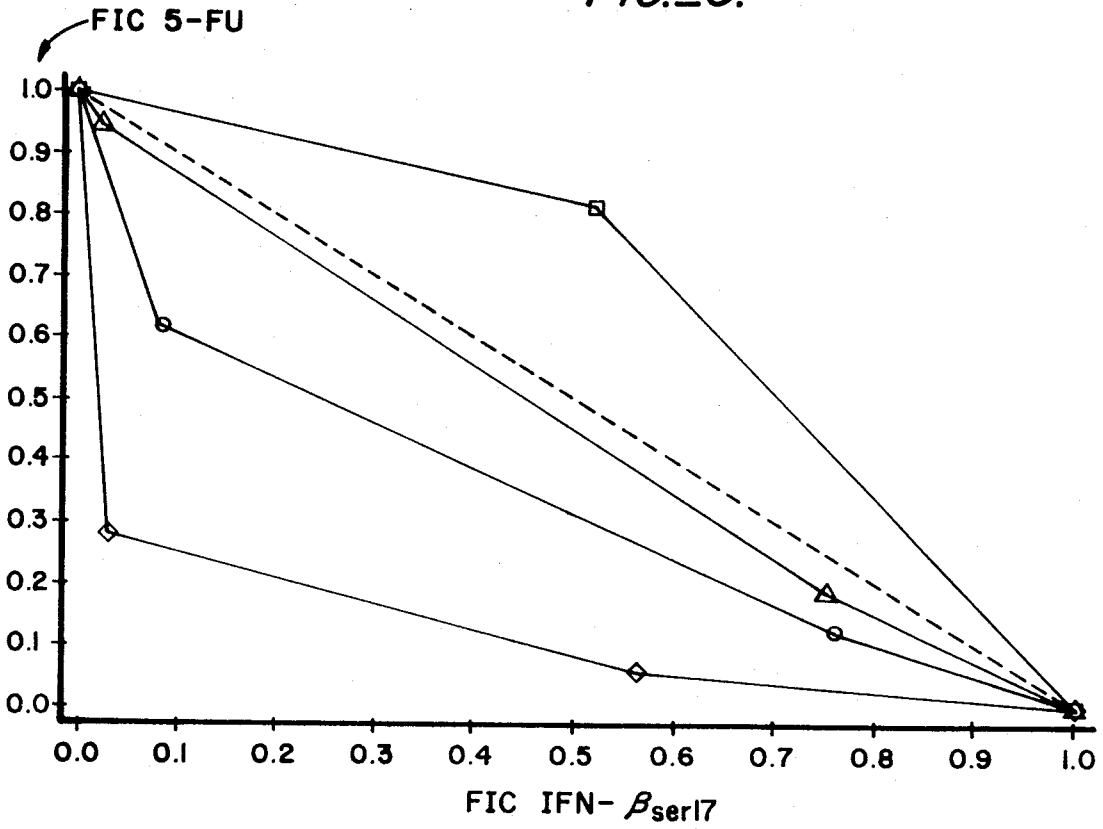
FIG. 6 is a series of isobolograms drawn from 7%, 19%, 30% and 42% cell growth inhibitory concentrations obtained from the dose response curves of FIG. 5 of 5-Fu and IFN-$\beta_{ser17}$, individually and in combinations, at 7% inhibition, OD=0.80 (open squares), 19% inhibition, OD=0.70 (open triangles), 30% inhibition, OD=0.60 (open dots), and 42% inhibition, OD=0.50 (open diamonds). The dashed line represents an additivity line under the broad definition of synergy described below. The axes were expressed in FIC indices units, where an FIC of 1.0 for IFN-$\beta_{ser17}$ corresponds to 9 IU/ml for open squares, 53 IU/ml for open triangles, 330 IU/ml for open dots and 3430 IU/ml for open diamonds, and where an FIC of 1.0 for 5- Fu corresponds to 0.020 $\mu$g/ml for open squares 0.084 $\mu$g/ml for open triangles, 0.13 $\mu$g/ml for open dots and 0.29 $\mu$g/ml for open diamonds.

The dose response curves for ZR-75-1 cells are shown in FIG. 5 for six concentrations of 5-Fu (0 μg/ml, 0.016 μg/ml, 0.08 μg/ml, 0.4 μg/ml, 2 μg/ml and 10 μg/ml) using the same symbols as for FIG. 3. FIG. 6, which is a series of isobolograms for four different cell growth inhibitory concentrations, was drawn from FIG. 5. In this figure values on the axes are expressed as absolute concentrations of components and as fractional inhibitory concentrations (FIC). As the present inhibition increased from 7% (open squares) to 42% (open diamonds), the combination changed from antagonistic to synergistic. Extrapolating the results to 50% inhibition shows that the combination of IFN-$\beta_{ser17}$ and 5-Fu was synergistic under both the broad and stricter definitions.

The interaction indices shown in Table 3 confirm the demonstration of synergy shown in the isobologram for most of the dose levels.

TABLE 3

| Interaction Indices Calculated for ZR-75-1* | | | | | | | |
|---|---|---|---|---|---|---|---|
| Dose of 5-Fu in Combination (μg/ml) | Dose of IFN-$\beta_{ser17}$ in Combination (IU/ml) | | | | | | |
| | 3 | 8 | 25 | 75 | 225 | 670 | 2000 6000 |
| 0.016 | 2.0 | 1.0 | 0.92 | 1.0 | 0.87 | 0.76 | 0.68 |
| 0.08 | 0.75 | 0.64 | 0.70 | 0.47 | <0.32 | <0.38 | <0.57 |
| 0.4 | 0.44 | 0.40 | 0.31 | 0.20 | 0.17 | <0.20 | <0.45 |
| 2 | 0.50 | 0.50 | 0.50 | 0.26 | | <0.31 | |
| 10 | | | | | | | |

*>1 = antagonism; <1 = synergism; 1 = additive under broad test

EXAMPLE 3

This example shows the synergy of using 5-Fu and IFN-$\beta_{ser17}$ for the SK-BR-3 cell line.

Figure 7:
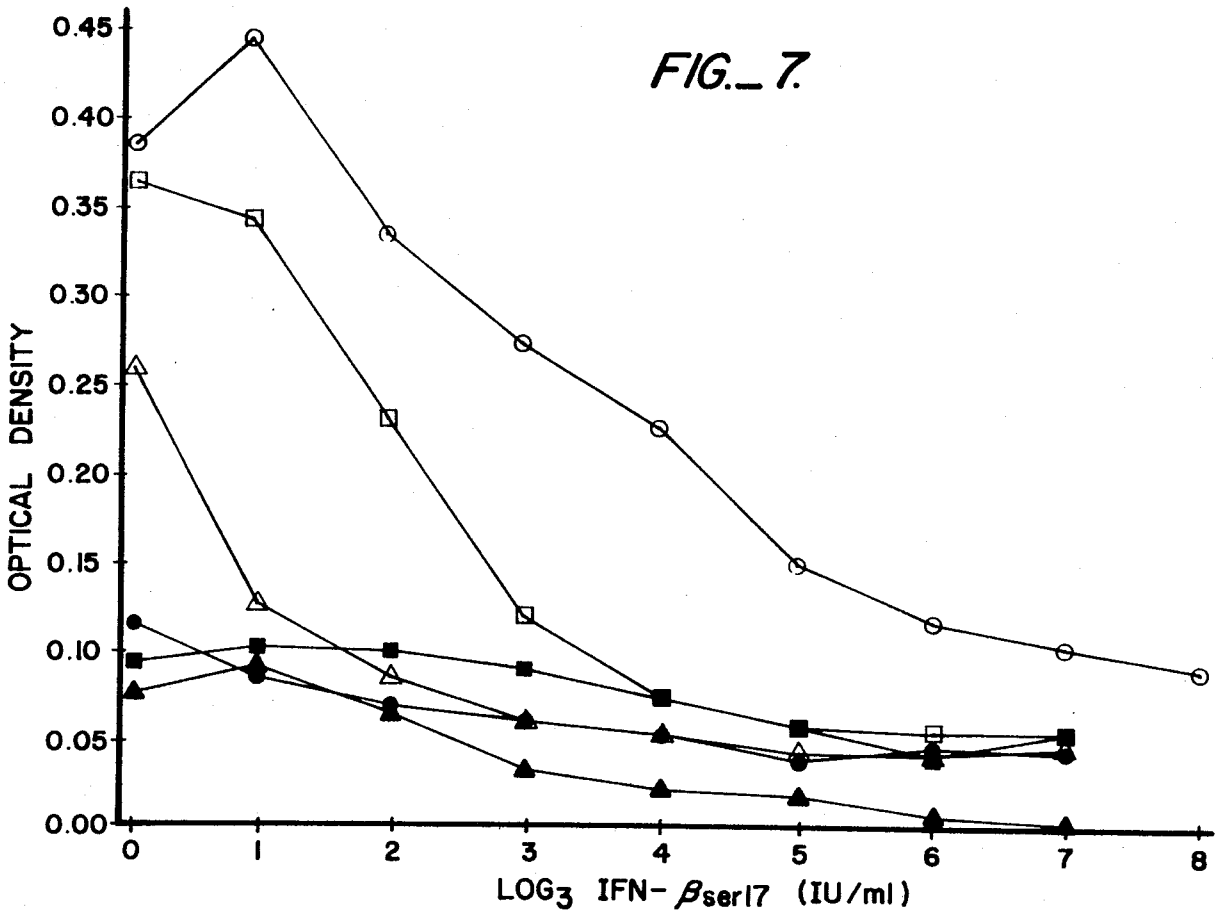
FIG. 7 is a series of dose response curves for SK-BR-3 cells. At three days after the cells were seeded, culture fluids were replaced with fresh media containing IFN-$\beta_{ser17}$ in combination with 0 $\mu$g/ml 5-Fu (open dots), 0.016 $\mu$g/ml 5-Fu (open squares), 0.08 $\mu$g/ml 5-Fu (open triangles), 0.4 $\mu$g/ml 5-Fu (solid dots), 2 $\mu$g/ml 5-Fu (solid squares), and 10 $\mu$g/ml 5-Fu (solid triangles). At six days after these combinations were added, the optical density of the media was measured.

A series of dose response curves for the SK-BR-3 cell line are shown in FIG. 7 for 5-Fu concentrations of 0, 0.016, 0.08, 0.4, 2 and 10 μg/ml (with the symbols the same as those described above).

Figure 8:
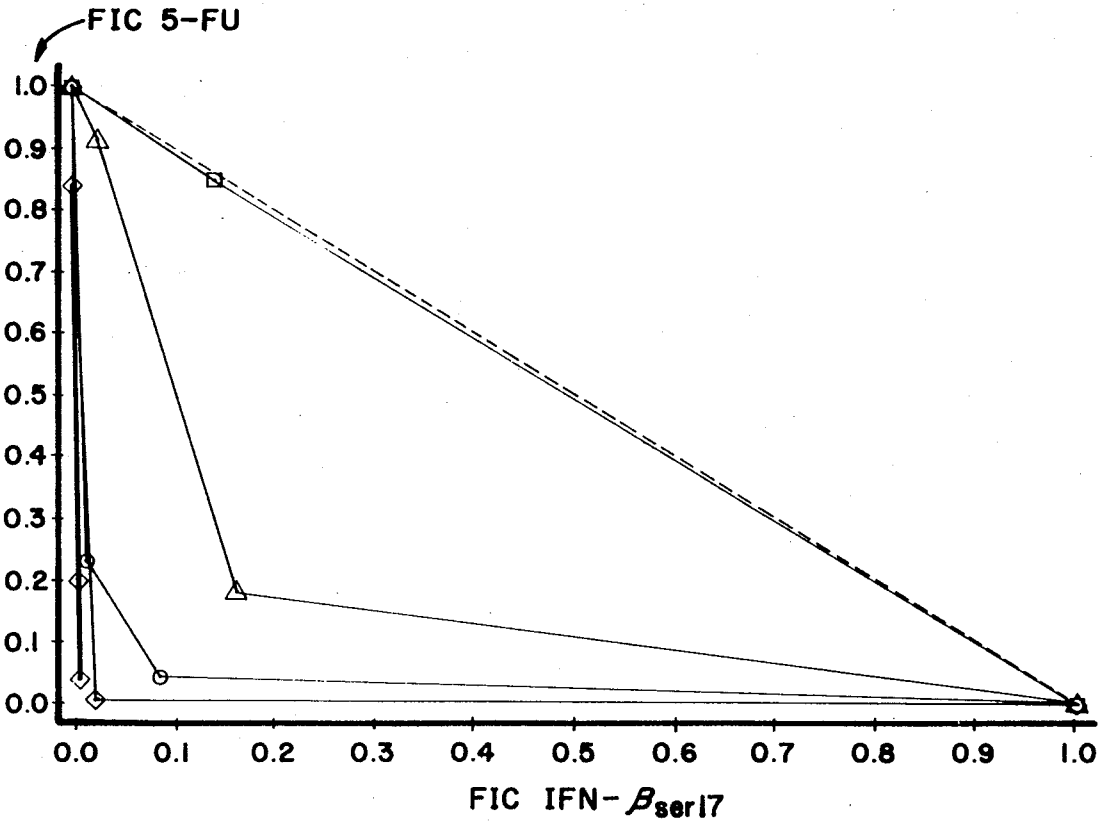
FIG. 8 is a series of isobolograms drawn from 9%, 25%, 61% and 70% cell growth inhibitory concentrations obtained from the dose response curves of FIG. 7 of 5-Fu and IFN-$\beta_{ser17}$, individually and in combinations, at 9% inhibition, OD=0.35 (open squares), 25% inhibition, OD=0.25 (open triangles), 61% inhibition, OD=0.15 (open dots), and 70% inhibition, OD=0.10 (open diamonds). The dashed line represents an additivity line under the broad definition of synergy described below. The axes are expressed in FIC indices units, where an FIC of 1.0 for IFN-$\beta_{ser17}$ corresponds to 7.7 IU/ml for open squares, 46 IU/ml for open triangles, 240 IU/ml for open dots and 2370 IU/ml for open diamonds, and where an FIC of 1.0 for 5-Fu corresponds to 0.019 $\mu$g/ml for open squares, 0.087 $\mu$g/ml for open triangles, 0.34 $\mu$g/ml for open dots and 1.7 $\mu$g/ml for open diamonds.

The isobolograms shown in FIG. 8 were drawn from FIG. 7 and show four different cell growth inhibitory concentrations. The axes represent absolute concentrations of components or FIC data as described in Example 2. As the percent inhibition increased from 9% (open squares) to 25% (open triangles) to 61% (open dots) to 70% (open diamonds), the combination became more synergistic. Extrapolating between the 25% and 61% inhibition curves it is seen that the combination of IFN-$\beta_{ser17}$ and 5-Fu is synergistic under both the broad and strict definitions.

The data in Table 4 confirm the demonstration of synergy shown in the isobolograms for all but one dose level.

TABLE 4

| Interaction Indices Calculated for SK-BR-3* | | | | | | | |
|---|---|---|---|---|---|---|---|
| Dose of 5-Fu in Combination (μg/ml) | Dose of IFN-$\beta_{ser17}$ in Combination (IU/ml) | | | | | | |
| | 3 | 8 | 25 | 75 | 220 | 670 | 2000 |
| 0.016 | 1.2 | 0.27 | 0.09 | <0.02 | | | |
| 0.08 | 0.25 | 0.02 | | | | | |
| 0.4 | 0.1 | 0.04 | | | | | |
| 2.0 | 10 | | | | | | |

*>1 = antagonism; <1 = synergism; 1 = additive under broad test

Table 5 is an equivalence table comparing doses of single agents with doses of combinations which give equivalent inhibition of growth.

TABLE 5

| Concentrations of IFN-$\beta_{ser17}$ and 5-Fu, Used Alone or in Combination with Each Other, Required to Produce Different Levels of Growth Inhibition of SK-BR-3 | | | | | |
|---|---|---|---|---|---|
| Percent Growth Inhibition Observed | Concentration Required When Agent Used Alone | | Concentrations Required When Agents Used in Combination | | Percent Growth Inhibition Expected If Combination Were Additive Under Broad Test |
| | IFN-β IU/ml | 5-Fu μg/ml | IFN-β IU/ml | 5-Fu μg/ml | |
| 9 | 7.6 | 0.019 | 1.1 | 0.016 | |
| 35 | 46 | 0.090 | 7.5 | 0.016 | |
| 35 | 46 | 0.090 | 1.1 | 0.08 | 33 |
| 61 | 240 | 0.34 | 20 | 0.016 | |
| 61 | 240 | 0.34 | 2.5 | 0.08 | |
| 74 | 2400 | 1.7 | 42 | 0.016 | 36 |
| 74 | 2400 | 1.7 | 6.3 | 0.08 | |
| 74 | 2400 | 1.7 | 1.7 | 0.40 | 70 |

TABLE 5-continued

| Percent Growth Inhibition Observed | Concentrations of IFN-$\beta_{ser17}$ and 5-Fu, Used Alone or in Combination with Each Other, Required to Produce Different Levels of Growth Inhibition of SK-BR-3: Concentration Required When Agent Used Alone: IFN-$\beta$ IU/ml | 5-Fu $\mu$g/ml | Concentrations Required When Agents Used in Combination: IFN-$\beta$ IU/ml | 5-Fu $\mu$g/ml | Percent Growth Inhibition Expected If Combination Were Additive Under Broad Test |
|---|---|---|---|---|---|
| 74 | 2400 | 1.7 | 9 | 2.0 | |

TABLE 7-continued

| Percent Growth Inhibition Observed | Concentrations of IFN-$\beta_{ser17}$ and 5-Fu, Used Alone or in Combination with Each Other, Required to Produce Different Levels of Growth Inhibition of Hs294T: Concentration Required When Agent Used Alone: IFN-$\beta$ IU/ml | 5-Fu $\mu$g/ml | Concentrations Required When Agents Used in Combination: IFN-$\beta$ IU/ml | 5-Fu $\mu$g/ml | Percent Growth Inhibition Expected If Combination Were Additive Under Broad Test |
|---|---|---|---|---|---|
| 72 | 1000 | 8 | 742 | 0.10 | |

EXAMPLE 4

This example shows the synergy of a combination of 5-Fu and IFN-$\beta_{ser17}$ for Hs294T cells.

Figure 9:
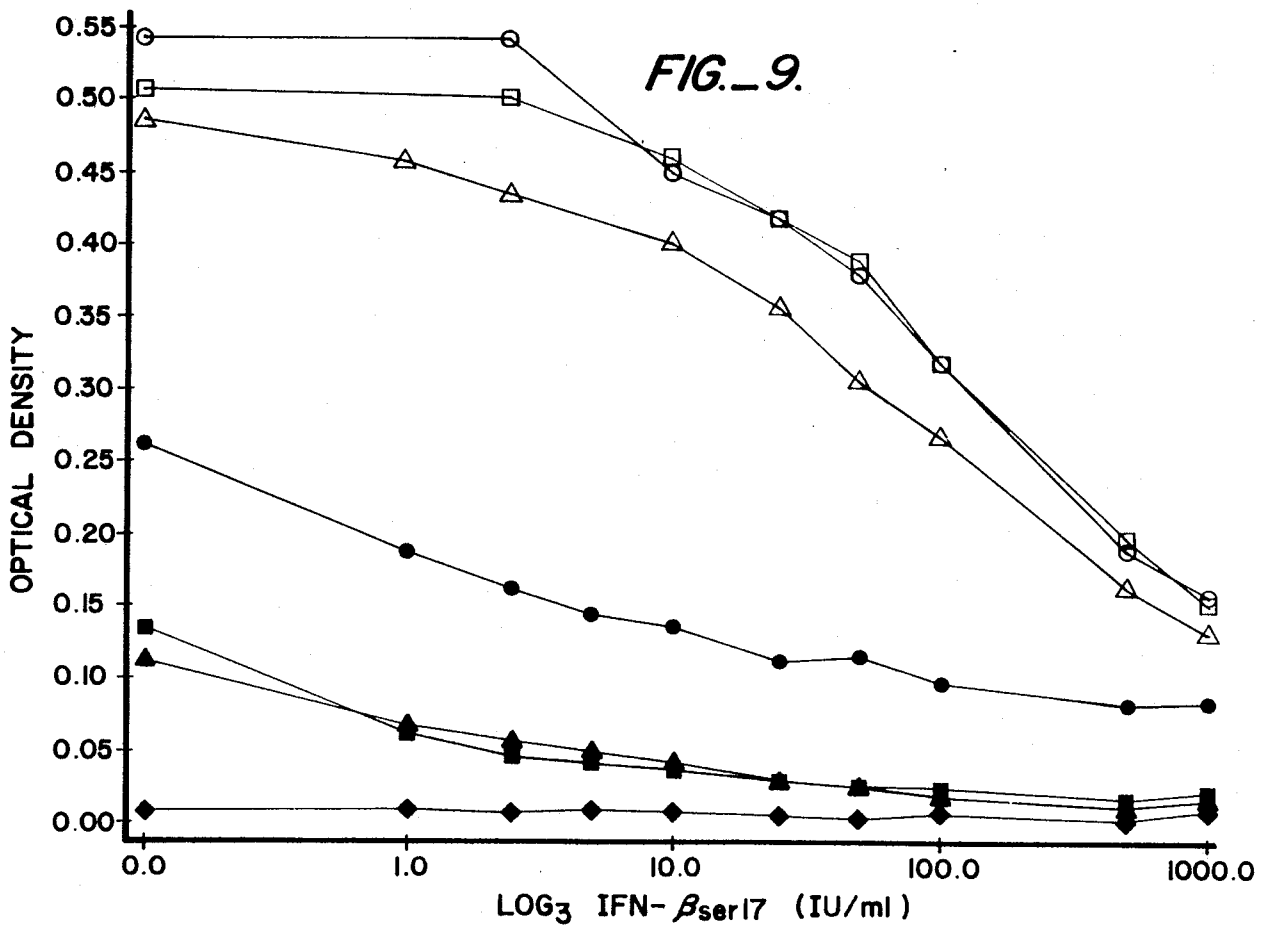
FIG. 9 is a series of dose response curves for Hs294T cells. At three days after the cells were seeded, culture fluids were replaced with fresh media containing IFN-$\beta_{ser17}$ in combination with 0 $\mu$g/ml 5-Fu (open dots), 0.01 $\mu$g/ml 5-Fu (open squares), 0.1 $\mu$g/ml (open triangles), 1 $\mu$g/ml 5-Fu (solid dots), 10 $\mu$g/ml 5-Fu (solid squares), 100 $\mu$g/ml 5-Fu (solid triangles), and 1000 $\mu$g/ml 5-Fu (solid diamonds). At six days after these combinations were added, the optical density of the media was measured.
Figure 10:
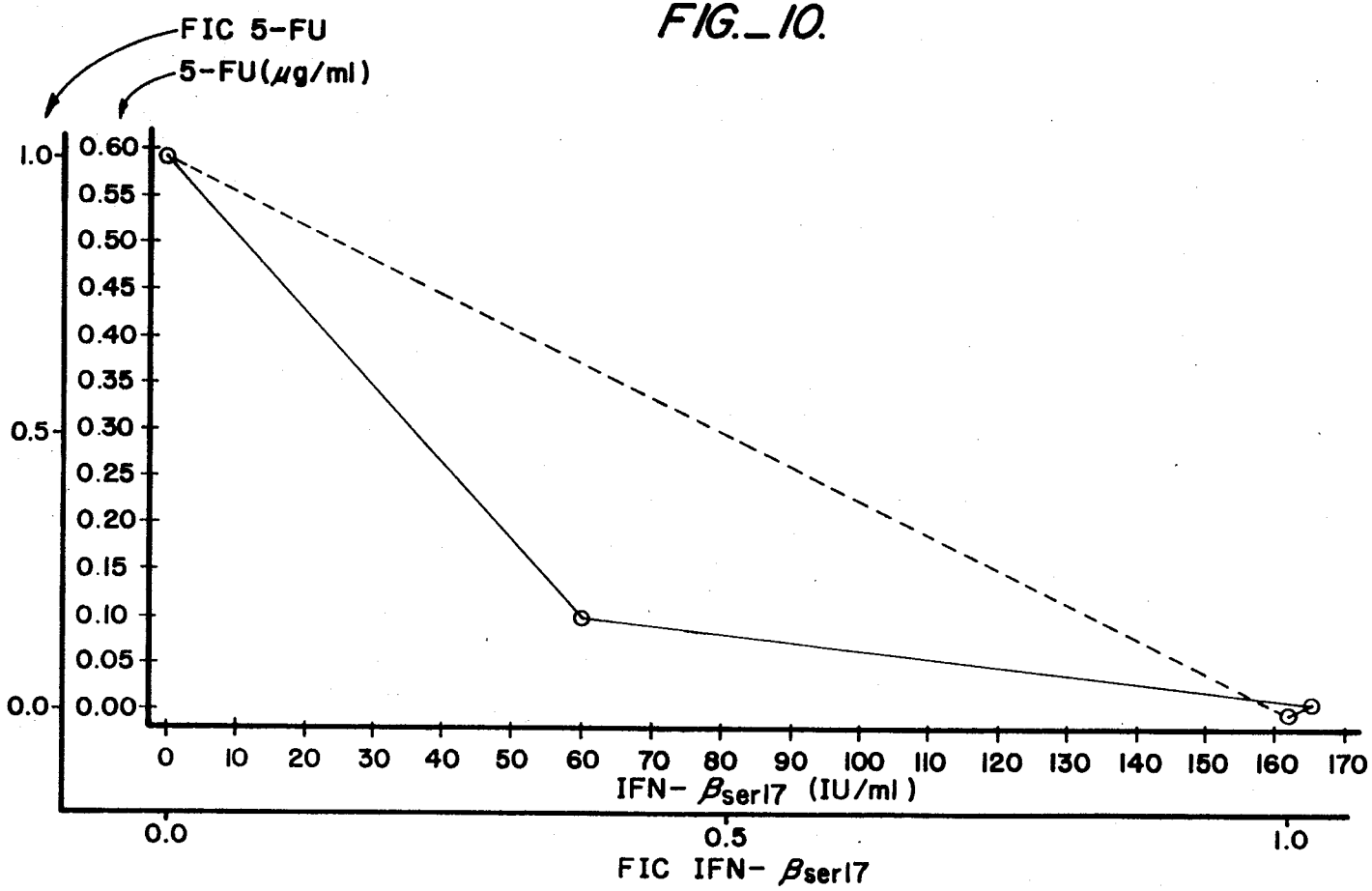
FIG. 10 is an isobologram drawn from 45% cell growth inhibitory concentrations obtained from the dose response curves of FIG. 9 of 5-Fu and IFN-$\beta_{ser17}$, individually and in combination (open dots). The dashed line represents an additivity line under the broad definition of synergy described below, with open dots below the line indicating synergy. The axes indicate both actual amounts of IFN-$\beta_{ser17}$ and 5-Fu and the FIC indices to which they correspond.
Figure 11:
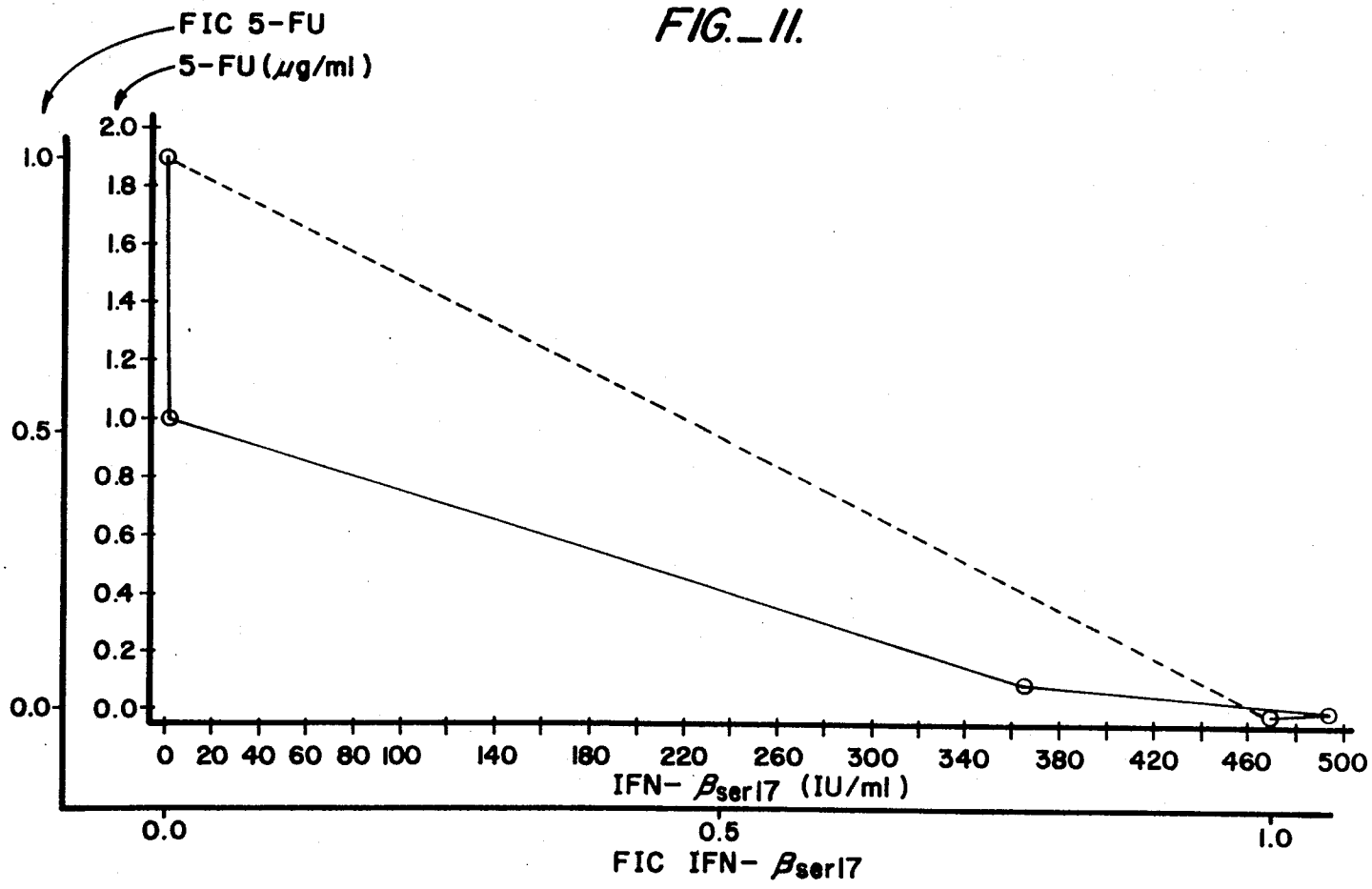
FIG. 11 is an isobologram drawn from 63% cell growth inhibitory concentrations obtained from the dose response curves of FIG. 9 of 5-Fu and IFN-$\beta_{ser17}$, individually and in combinations (open dots). The dashed line represents an additivity line under the broad definition of synergy described below, with open dots below the line indicating synergy. The axes indicate both actual amounts of IFN-$\beta_{ser17}$ and 5-Fu and the FIC indices to which they correspond.
Figure 12:
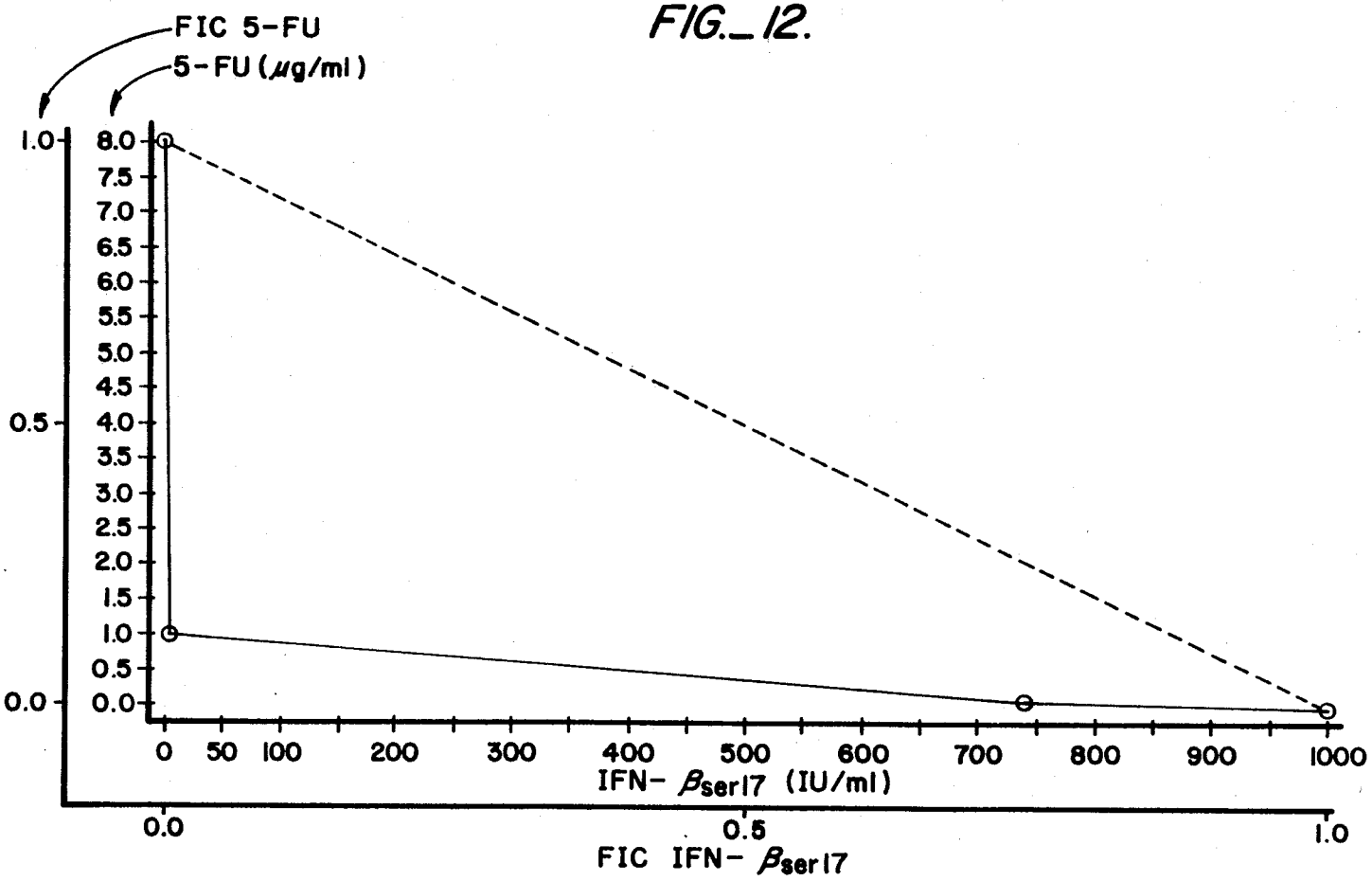
FIG. 12 is an isobologram drawn from 72% cell growth inhibitory concentrations obtained from the dose response curves of FIG. 9 of 5-Fu and IFN-$\beta_{ser17}$, individually and in combinations (open dots). The dashed line represents an additivity line under the broad definition of synergy described below, with open dots below the line indicating synergy. The axes indicate both actual amounts of IFN-$\beta_{ser17}$ and 5-Fu and the FIC indices to which they correspond.

The dose response curves for the Hs294T cell line are shown in FIG. 9 for concentrations of 5-Fu of 0, 0.01, 0.1, 1, 10, 100 and 1000 $\mu$g/ml with the 0, 0.01 and 0.1 concentrations represented by open characters of dots, squares and triangles, respectively, and the 1, 10, 100, and 1000 concentrations represented by solid dots, squares, triangles and diamonds, respectively. Figs. 10–12 illustrate the isobolograms drawn from these dose response curves at 45%, 63% and 72% growth inhibition respectively. The axes contain both absolute concentrations of components and FIC indices. Each of the isobolograms shows synergy of the combinations under the broad definition, extrapolated to 50% inhibition, but not under the strict definition. Table 6 confirms the synergistic results for many dose levels.

TABLE 6

| Dose of 5-Fu in Combination ($\mu$g/ml) | Interaction Indices Calculated for Hs294T*: Dose of IFN-$\beta_{ser17}$ in Combination (IU/ml): 1 | 2.5 | 5 | 10 | 25 | 50 | 100 | 500 | 1000 |
|---|---|---|---|---|---|---|---|---|---|
| 0.01 | 0.43 | >1 | 0.30 | 1.2 | 1.0 | 1.2 | >1 | >1 | >1 |
| 0.01 | | 0.74 | 0.50 | 0.72 | 0.67 | 0.58 | 0.64 | 0.61 | |
| 1 | | 0.27 | 0.17 | | | | | | |
| 10 | | | | | | | | | |
| 100 | | | | | | | | | |

*>1 = antagonism; <1 = synergism; 1 = additive effect under broad definition

Table 7 is an equivalence table comparing doses of single agents with doses of combinations which give equivalent inhibition of growth.

TABLE 7

| Percent Growth Inhibition Observed | Concentrations of IFN-$\beta_{ser17}$ and 5-Fu, Used Alone or in Combination with Each Other, Required to Produce Different Levels of Growth Inhibition of Hs294T: Concentration Required When Agent Used Alone: IFN-$\beta$ IU/ml | 5-Fu $\mu$g/ml | Concentrations Required When Agents Used in Combination: IFN-$\beta$ IU/ml | 5-Fu $\mu$g/ml | Percent Growth Inhibition Expected If Combination Were Additive Under Broad Test |
|---|---|---|---|---|---|
| 8 | 5.8 | 0.14 | 2.8 | 0.010 | |
| 26 | 37 | 0.16 | 10 | 1.10 | |
| 26 | 37 | 0.16 | 41 | 0.010 | |
| 45 | 162 | 0.59 | 60 | 0.10 | |
| 45 | 162 | 0.59 | 166 | 0.010 | |
| 63 | 469 | 1.9 | 0.9 | 1.0 | |
| 63 | 469 | 1.9 | 365 | 0.10 | |
| 63 | 469 | 1.9 | 493 | 0.010 | |
| 72 | 1000 | 8 | 4.4 | 1.0 | |

EXAMPLE 5

This example shows that the combination of 5-Fu and IFN-$\beta_{ser17}$ is synergistic for the BT-20 cell line.

Figure 13:
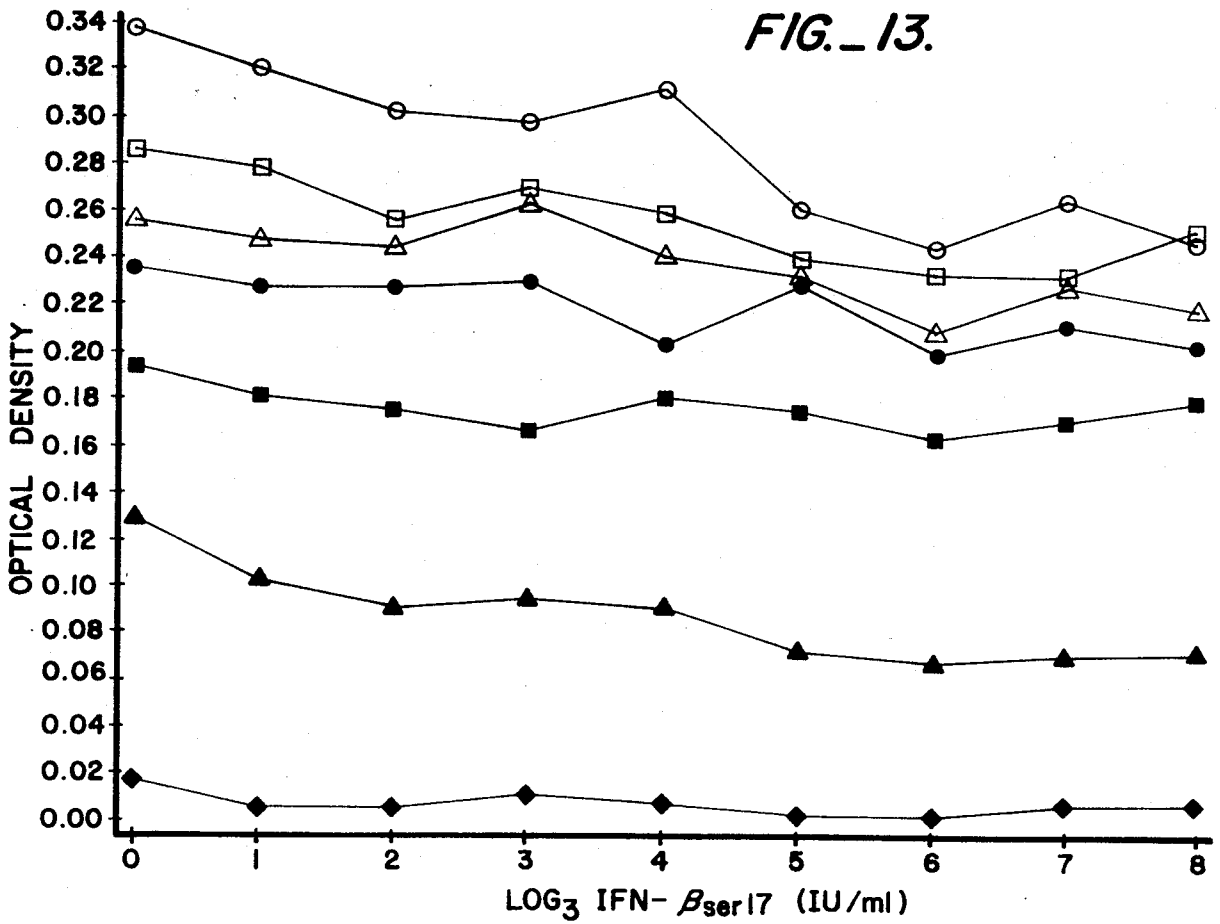
FIG. 13 is a series of dose response curves for BT-20 cells. At three days after the cells were seeded, culture fluids were replaced with fresh media containing IFN-$\beta_{ser17}$ in combination with 0 μg/ml 5-Fu (open dots), 0.016 μg/ml 5-Fu (open squares), 0.08 μg/ml (open triangles), 0.4 μg/ml 5-Fu (solid dots), 2 μg/ml 5-Fu (solid squares), 10 μg/ml 5-Fu (solid triangles), and 100 μg/ml 5-Fu (solid diamonds). At six days after the combinations were added, the optical density of the media was measured.

Dose response curves drawn for the BT-20 cell line using 5-Fu concentrations of 0, 0.016, 0.08, 0.4, 2, 10 and 100 $\mu$g/ml are shown in FIG. 13, with the 0, 0.016 and 0.08 concentrations represented by open dots, squares and triangles, respectively, and the 0.4, 2, 10 and 100 concentrations represented by solid dots, squares, triangles and diamonds, respectively.

Figure 14:
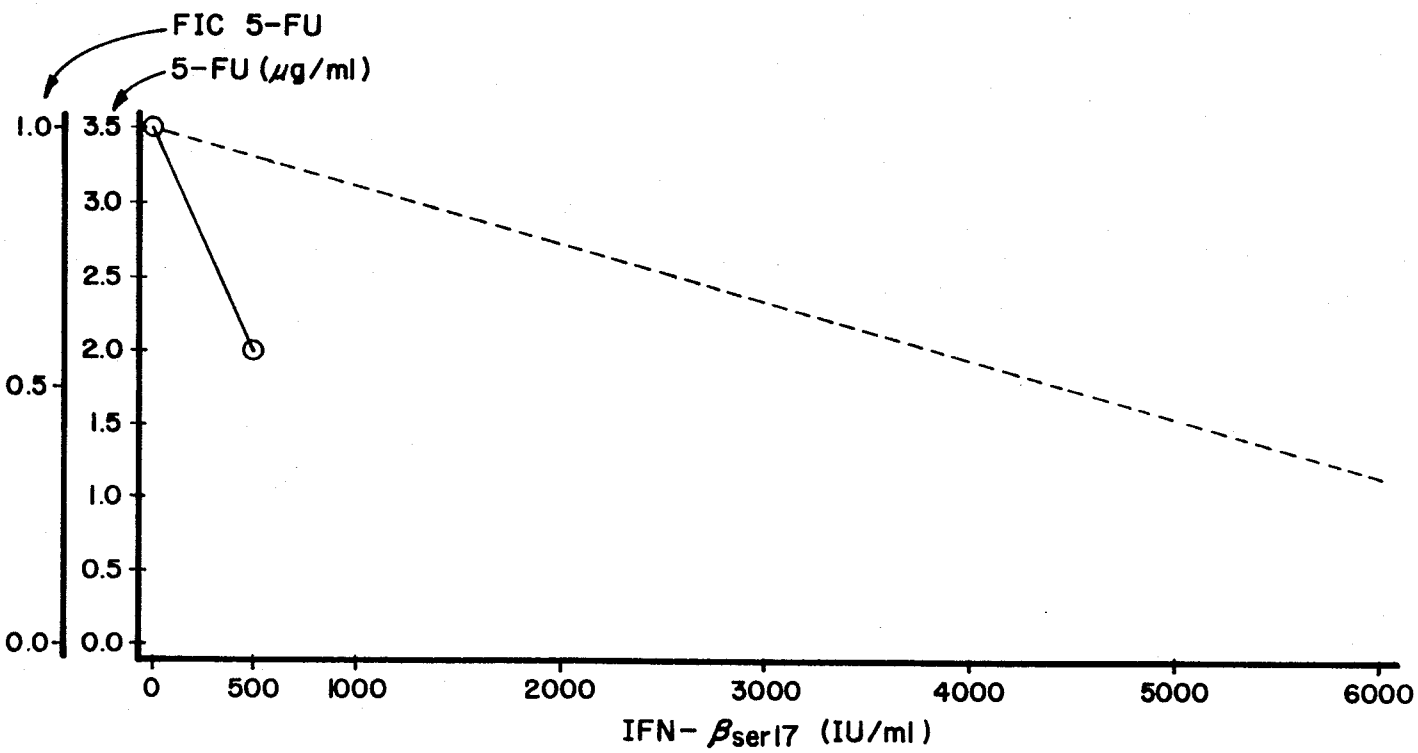
FIG. 14 is an isobologram drawn from 50% cell growth inhibitory concentrations obtained from the dose response curves of FIG. 13 of 5-Fu and IFN-$\beta_{ser17}$, individually and in combinations (open dots). The dashed line represents an additivity line under the broad definition of synergy described below, with the open dot below the line indicating synergy. The axes indicate both the actual amounts of IFN-$\beta_{ser17}$ and 5-Fu and the FIC index for 5-Fu to which the actual amount corresponds. The FIC index for IFN-$\beta_{ser17}$ could not be determined because at the dosages used the 50% growth inhibitory effect could not be achieved. Therefore, it cannot be determined where exactly the dashed line intercepts the X-axis except that it does so at a point beyond 6000 IU/ml of IFN-$\beta_{ser17}$.

An isobologram at 50% cell growth inhibitory concentration drawn from the dose response curves is shown in FIG. 14. With the dosages used the 50% growth of the cell line could not be inhibited using IFN-$\beta_{ser17}$ alone (but could be inhibited with IFN-$\beta_{ser17}$ in combination with 5-Fu). Therefore, the FIC index for IFN-$\beta_{ser17}$ could not be determined, although it is known that the dashed line intercepts the x-axis above 6000 IU/ml IFN-$\beta_{ser17}$. The cell line appeared to be resistant to IFN-$\beta_{ser17}$ under the conditions under which the experiment was conducted. The dots, because they appear below the 1.0 FIC index for 5-Fu and thus below the dashed line, show that the combination is synergistic under the broad definition, but not under the stricter definition of synergy as defined herein.

EXAMPLE 6

This example illustrates the use of 5-Fu and IFN-$\beta_{ser17}$ on other breast carcinoma cell lines.

Dose response curves were prepared for the breast cancer cell lines BT-549, MCF-7, T47D and ZR-75-30, all available from ATCC, in which 5-Fu and IFN-$\beta_{ser17}$ were employed. The results indicated that no determination of synergy could be made with respect to any of these cell lines because 50% growth inhibition could not be obtained for any of these cell lines using IFN-$\beta_{ser17}$ alone or combinations of 5-Fu and IFN-$\beta_{ser17}$.

EXAMPLE 7

Three known therapeutic agents, doxorubicyn, methotrexate, and vincristine, were each used in combination with IFN-$\beta_{ser17}$ using the procedure of Example 1 for cell lines ZR-75-30, ZR-75-1, BT-20, SK-BR-3, BT-549, CaMa-1, MCF-7, and T47D.

With many of these cell lines no determination of snyergy could be made because 50% growth inhibition could not be obtained using IFN-$\beta_{ser17}$ alone or IFN-$\beta$ser17 in combination with 5-Fu. For some cell lines the effect was additive under the broad test. For one cell line, ZR75-1, using vincristine the effect was synergistic under the broad and stricter tests. For another cell line, MCF-7, using doxorubicyn the effect was synergistic under the broad and strict tests with moderate doses of doxorubicyn and low doses of IFN but not synergistic under the stricter test (but synergistic under the broader test) with low doses of doxorubicyn and high doses of IFN.

In summary, the present invention is seen to provide a combination therapy scheme where 5-Fu and recombinant $\beta$-IFN act in a synertistic cytotoxic manner against four breast cancer cell lines and one melanoma cell line, but not against four other breast cancer cell lines.

What is claimed is:

1. A process for preparing a composition having synergistic cytotoxic effect in breast cancer cell lines CaMa-1, SK-BR-3, BT-20 or ZR-75-1 or melanoma cell line Hs294T comprising combining a synergistically effective amount of 5-fluorouracil dependent on the cell line and a synergistically effective amount of recombinant human beta-interferon dependent on the cell line.

2. The process of claim 1 wherein the beta-interferon is produced from *E. coli* or Chinese hamster ovary cells.

3. The process of claim 1 wherein the beta-interferon is a synthetic mutein of beta-interferon having the cysteine residue at position 17 of beta-interferon replaced by a serine residue.

4. The process of claim 1 further comprising combining the 5-fluorouracil and interferon with a pharmaceutically acceptable diluent or carrier.

5. The process of claim 1 wherein the breast cancer cell line is CaMa-1, SK-BR-3 or ZR-75-1.

6. A composition having synergistic cytotoxic effect in breast cancer cell lines CaMa-1, SK-BR-3, BT-20 or ZR-75-1 or melanoma cell line Hs294T comprising a synergistically effective amount of 5-fluorouracil dependent on the cell line and a synergistically effective amount of recombinant human beta-interferon dependent on the cell line.

7. The composition of claim 6 wherein the beta-interferon is produced from *E. coli* or Chinese hamster ovary cells.

8. The composition of claim 6 wherein the beta-interferon is a mutein of beta-interferon having the cysteine residue at position 17 of beta-interferon replaced by a serine residue.

9. The composition of claim 6 wherein the breast cancer cell line is CaMa-1, SK-BR-3 or ZR-75-1.

10. In a process for treating human breast cancer or myeloma with a composition of matter containing human beta-interferon, the improvement which comprises treating tissue cultures of cell lines CaMa-1, ZR-75-1, BT-20, Hs294T or SK-BR-3 with a substantially pharmaceutically pure composition having synergistic cytotoxic effect comprising a synergistically effective amount of 5-fluorouracil dependent on the cell line and a synergistically effective amount of recombinant beta-interferon dependent on the cell line.

11. The process of claim 10 wherein the beta-interferon is produced from *E. coli* or Chinese hamster ovary cells.

12. The process of claim 10 wherein the beta-interferon is a mutein having the cysteine residue at position 17 of beta-interferon replaced by a serine residue.

13. The process of claim 10 wherein the composition further comprises a pharmaceutically acceptable diluent or carrier.

14. The process of claim 10 wherein the cell line is CaMa-1, ZR-75-1 or SK-BR-3.

15. A pharmaceutical composition having synergistic cytotoxic effect of breast cancer cell lines CaMa-1, SK-BR-3, BT-20 or ZR-75-1 or melanoma cell line Hs294T comprising a synergistically effective amount of 5-fluorouracil dependent on the cell line, a synergistically effective amount of recombinant human beta-interferon dependent on the cell line, and an effective amount of a pharmaceutically acceptable diluent.

16. The composition of claim 15 wherein the beta-interferon is produced from *E. coli* or Chinese hamster ovary cells.

17. The composition of claim 15 wherein the beta-interferon is a mutein having the cysteine residue at position 17 of beta-interferon replaced by a serine residue.

18. The composition of claim 15 wherein the breast cancer cell line is CaMa-1, SK-BR-3 or ZR-75-1.

* * * * *